(12) United States Patent
Yadav et al.

(10) Patent No.: US 6,632,980 B1
(45) Date of Patent: *Oct. 14, 2003

(54) BINARY VIRAL EXPRESSION SYSTEM IN PLANTS

(75) Inventors: Narendra S. Yadav, Chadds Ford, PA (US); S. Carl Falco, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/442,021

(22) Filed: Nov. 17, 1999

Related U.S. Application Data

(63) Continuation-in-part of application No. 09/178,089, filed on Oct. 23, 1998, now Pat. No. 6,077,992.
(60) Provisional application No. 60/150,255, filed on Aug. 23, 1999, provisional application No. 60/130,086, filed on Apr. 20, 1999, and provisional application No. 60/063,504, filed on Oct. 24, 1997.

(51) Int. Cl.⁷ .................. C12N 15/82; C12N 15/90; C12N 5/04; A01H 1/00; A01H 5/00
(52) U.S. Cl. .................. 800/278; 435/320.1; 435/468; 800/280; 800/285; 800/287; 800/298; 800/301
(58) Field of Search .................. 435/320.1, 69.1, 435/468, 410, 418, 419, 69.8; 800/278, 279, 280, 287, 288, 295, 298, 300, 301, 302, 285

(56) References Cited

U.S. PATENT DOCUMENTS

| | | | |
|---|---|---|---|
| 4,855,237 A | 8/1989 | Morinaga et al. | 435/320.1 |
| 5,658,772 A | 8/1997 | Odell et al. | 435/468 |
| 5,723,765 A | 3/1998 | Oliver et al. | 800/278 |
| 5,910,415 A | 6/1999 | Hodges et al. | 435/6 |
| 5,925,808 A | 7/1999 | Oliver et al. | 800/298 |
| 5,929,307 A | 7/1999 | Hodges et al. | 800/303 |
| 5,965,791 A | 10/1999 | Ebinuma et al. | 800/278 |
| 5,977,441 A | 11/1999 | Oliver et al. | 800/298 |
| 2002/0147168 A1 * | 10/2002 | Surin et al. | 514/44 |

FOREIGN PATENT DOCUMENTS

| | | | | |
|---|---|---|---|---|
| EP | 221044 A1 | 5/1987 | ............ | C12N/15/00 |
| EP | 0 425 004 A | 5/1991 | ............ | C12N/15/40 |
| EP | 0425044 A2 | 5/1991 | ............ | C12N/15/40 |
| EP | 221044 | 5/1997 | ............ | C12N/15/00 |
| WO | WO 91/09957 A1 | 7/1991 | ............ | C12N/15/82 |
| WO | WO 93/01283 A1 | 1/1993 | ............ | C12N/15/00 |
| WO | WO 94/03619 A2 | 2/1994 | ............ | C12N/15/82 |
| WO | WO 94 19477 A | 9/1994 | ............ | C12N/15/82 |
| WO | WO 94/19477 | 9/1994 | ............ | C12N/15/82 |
| WO | WO 95 25801 A | 9/1995 | ............ | C12N/15/82 |
| WO | WO 9534668 | 12/1995 | ............ | C12N/15/83 |
| WO | WO 95/34668 A2 | 12/1995 | ............ | C12N/15/83 |
| WO | WO 9604393 A | 2/1996 | | |
| WO | WO 97/06269 A1 | 2/1997 | ............ | C12N/15/82 |
| WO | WO 97/11189 A2 | 3/1997 | ............ | C12N/15/82 |
| WO | WO 97/37012 A1 | 10/1997 | ............ | C12N/15/11 |
| WO | WO9737012 A1 | 10/1997 | ............ | C12N/15/11 |
| WO | WO 98 28431 | 7/1998 | ............ | C12N/15/82 |
| WO | WO 98/36083 A1 | 8/1998 | ............ | C12N/15/82 |
| WO | WO 9836083 | 8/1998 | ............ | C12N/15/82 |
| WO | WO 98/38323 A2 | 9/1998 | ............ | C12N/15/82 |
| WO | WO 99/11807 A1 | 3/1999 | ............ | C12N/15/82 |
| WO | WO 99/25840 A1 | 5/1999 | ............ | C12N/15/52 |
| WO | WO 99/25841 A1 | 5/1999 | ............ | C12N/15/52 |
| WO | WO 99/25854 A1 | 5/1999 | ............ | C12N/15/82 |
| WO | WO 99 25855 A | 5/1999 | ............ | C12N/15/83 |
| WO | WO 00/17365 | 3/2000 | | |
| WO | WO 00/17365 A2 | 3/2000 | ............ | C12N/15/34 |
| WO | WO 00/60091 A2 | 10/2000 | ............ | C12N/15/52 |

OTHER PUBLICATIONS

Marja C. P. Timmermans et al., Geminiviruses and their uses as extrachromosomal replicons, Annu. Rev. Plant Physiol. Plant Mol. Biol. 1994, 45 pp. 79–112.*

Angell et al., Consistant gene silencing in transgenic plants expressing a replication potato virus X RNA, *EMBO Journal*, 3675–84, Jun. 1997.

Hong et al., Transactivation of dianthin transgene expression by African cassava mosaic virus AC2, *Virology, US, Academic Press, Orlando*, vol. 228, No. 2, 383–387, Feb. 17, 1997.

Pruss et al., Plant viral synergism: The potyviral genome encodes a brand–range pathogenicity enhance that transactivates replication of heterologous viruses. Plant Cell, vol. 9, 1997 pp. 859–868.

Covey, S. N. et. al., 1997 Nature (London) vol. 385: pp. 781–782.

Kumagai et al., 1995, Proc. Natl. Acad. Sci. (U.S.A.) vol. 92: pp. 1679–1683.

Ratcliff, F. et al., 1997, Science (Washington, D.C.) vol. 276: pp. 1558–1560.

DeVeylder, L. et al., Plant Cell Physiol., vol. 38, pp. 568–577, 1997.

Gatz, C., Annu. Rev. Plant Physiol. Plant Mol. Biol., vol. 48: pp. 89–108, 1997.

Hansen, G. et al., Mol. Gen. Genet. vol. 254: pp. 337–343, 1997.

Odell, J. et al., Plant Physiol. 91994, vol. 106: 447–458.

(List continued on next page.)

*Primary Examiner*—Ashwin Mehta

(57) ABSTRACT

The invention relates to two plant transgene expression systems. The first is comprised of two chromosomally-integrated components that are individually heritable. One component is an inactive replicon, which contains cis-acting viral sequences required for replication and is unable to replicate episomally. The other component is a chimeric transactivating gene comprising a regulated promoter operably-linked to the coding region for a protein that can transactivate replicon replication. Regulated expression of the transactivation protein in plant cells containing the inactive replicon triggers release of free replicon from the integrated inactive replicon and allows episomal replication.

25 Claims, 7 Drawing Sheets

OTHER PUBLICATIONS vander Geest et al., Plant Physiol., 1995, 109(4), pp. 1151–1158.

Ma et al., Aust. J. Plant Physiol., 1998, 25(1), pp. 53–59.

Czako et al., Mol. Gen. Genet., 1992, vol. 235(1), pp. 33–40.

Albert et al., Plant J. vol. 7: pp. 649–659, 1995.

Araki et al., Nucleic Acids Res. vol. 25: 868–872, 1997.

McGonigle, Brian et al., Nuclear localization of the Arabidopsis APETALA3 and PISTILLATA homeotic gene product depends on their simultaneous expression, Genes and Development, vol. 10, No. 14, 1996, pp. 1812–1821.

Theerakulpisut, P. et al., Isolation and Development Expression of BCP1 an Anther–Specific CDNA Clone in Brassica–Campestris, Plant Cell, vol. 3, No. 10, 1991, pp. 1073–1084.

Ow, The Right Chemistry for Marker Gene Removal, Nature Biotechnology, vol. 19, Feb. 2001 pp. 115–116.

Russell et al., Mol. Gen. Genet. vol. 234: pp. 49–59, 1992.

N. L. Craig, Annu. Rev. Genet, vol. 22: pp. 77–105, 1998.

Lyznik et al., FLP–mediated recombination of FRT sites in the maize genome Nucleic Acids Research, 1996, vol., 24, No. 19, pp. 3784–3789.

Kilby et al. FLP recombinases in transgenic plants: Constitutive activity in stably transformed tobacco and generation of marked cells clones in Arabidopsis, Plant Journal, 1995, vol. 8, No. 5, pp. 637–652.

Odell et al., Site–directed Recombination in the Genome of Transgenic Tobacco, Mol. Gen. Genet, 1990 223 (3), 369–378.

Onouchi et al., Operation of an efficient site–specific recombination system in Zygosaccharomyces rouxii in tobacco cells, Necleic Acids Res., 1991, 19, 23, 6373–6378.

Odell et al., Use of site–specific recombination systems in plants. Homologous Recomb. Gene Silencing Plants (1994), 219–70, Editors: Paszkowski, Jerzy, Publisher: Kluwer, Dordrecht, Germany.

Zubko et al., (2000) Nature Biotechnology 18:442.

Groth et al., (2000) Proc. Natl Acad Sci. USA 97:5995.

H Matsuzaki et al., J. Bacteriology, vol. 172, p. 610, 1990.

Sablowski et al., Proc. Natl. Acad. Sci. USA, vol. 92, pp. 6901–6905, 1995.

Hayes et al., Nucleic Acids Res., vol. 17, pp. 2391–2403, 1989.

Hayes et al., Nature (London), vol. 334, pp. 179–182, 1988.

Hong et al., Resistance to geminivirus infection by virus–induced expression of dianthin in transgenic plants., Virology, 1996 Jun. 1, vol. 220, pp. 119–127.

Hong et al., "Transactivation of dianthin transgene expression by African cassava mosaic virus AC2.", Virology, (Feb. 17, 1997, vol. 228, pp. 383–387).

Rogers et al., Cell, vol. 45, pp. 593–600, 1986.

Goodman, J. Gen. Virol., vol. 54, pp. 9–21, 1981.

Hanley–Bowdin et al., Plant Cell, vol. 1, pp. 1057–1067, 1989.

Hanley–Bowdoin et al., Proc. Natl. Acad. Sci. U.S.A., vol. 87, pp. 1446–1450, 1990.

Hayes et al., Nucleic Acids Res., vol. 17, pp. 10213–10222, 1989.

Al–Kaff et al., Science (Washington, DC), vol. 279, pp. 2113–2115, 1998.

Needham et al., Plant Cell Rep., vol. 17, pp. 631–639, 1998.

Senior et al., Biotechnol. Genet. Eng. Rev., vol. 15, pp. 79–119, 19980

Thomas et al., Plant Growth Regul., vol. 25, pp. 205, 1998, Book Review.

Ruiz et al., Plant Cell, vol. 10, pp. 937–946, 1998.

Kjemtrup et al., Plant J., vol. 14, pp. 91–100, 1998.

Atkinson et al., Plant J., vol. 15, pp. 593–604, 1998.

Mariani et al., Induction of Male Sterility in Plants by a Chimaeric Ribonuclease Gene, Nature GB MacMillan Journals LTD, London, vol. 347, Oct. 25, 1990 pp. 737–741.

Hayes et al., Replication of tomato golden mosaic virus DNA B in transgenic expressing open reading frames (ORFs) of DNA A: ,Nucleic Acids Research, GB, Oxford University Press, Surrey, vol. 17, No. 24, 10213–10222, Dec. 25, 1989.

* cited by examiner

*Proreplicon:* ori     Coat protein or target gene     ori

↓ Regulated Expression of Replication protein

*Replicon replicating in trans:*     ori

Coat protein or target gene

Trait Gene Expression and Removal Are Unlinked

*STAGE 1 (Germination):*

*STAGE 2 (Trait expression):*

*STAGE 3 (Post-trait expression):*

Trait Expression And Removal Are Linked

*STAGE 1 (Germination):*

*STAGE 2 (Trait expression):*

*STAGE 3 (Post-trait expression):*

BINARY VIRAL EXPRESSION SYSTEM IN PLANTS

This application is a continuation-in-part of U.S. application Ser. No. 09/178,089 filed Oct. 23, 1998, now U.S. Pat. No. 6,077,992, which claims the benefit of U.S. Provisional Application No. 60/063,504, filed Oct. 24, 1997. This application further claims the benefit of U.S. Provisional Application No. 60/150,255 filed Aug. 23, 1999, and U.S. Provisional Application No. 60/130,086 filed Apr. 20, 1999.

FIELD OF INVENTION

The present invention relates to the field of molecular biology and the genetic transformation of plants with foreign gene fragments. More particularly, the invention relates to a binary expression system useful for conditionally expressing transgenes in plants.

BACKGROUND OF THE INVENTION

Two serious technical problems beset plant transgenics. First, plant transgene expression attains only low and inconsistent levels. These poor expression levels are attributable in part to random chromosomal integration ('position effects') and in part to a general lack of gene copy number-dependent expression. Episomal vectors are expected to overcome these problems. In constrast to plants, microbes can attain high-level expression through episomal (plasmid) vectors because these vectors can be maintained by selection. Although plant viruses have been used as episomal expression vectors, their use has been restricted to transient expression because of lack of selection and/or their cellular toxicity (U.S. Pat. No. 4,855,237, WO 9534668).

Second, non-specific expression of transgenes in non-desired cells and tissues hinders plant transgenic work. This is important where the goal is to produce high levels of phytotoxic materials in transgenic plants. Conditional transgene expression will enable economic production of desired chemicals, monomers, and polymers at levels likely to be phytotoxic to growing plants by restricting their production to production tissue of transgenic plants either just prior to or after harvest. Therefore, lack of a commercially usable conditional expression system and the difficulty in attaining a reliable, high-level expression both limit development of transgene expression in plants.

Plant Viruses

Viruses are infectious agents with relatively simple organization and unique modes of replication. A given plant virus may contain either RNA or DNA, and may be either single- or double-stranded.

RNA Plant Viruses

Double-stranded RNA plant viruses include rice dwarf virus (RDV) and wound tumor virus (WTV). Single-stranded RNA plant viruses include tobacco mosaic virus (TMV) and potato virus X (PVX), turnip yellow mosaic virus (TYMV), rice necrosis virus (RNV) and brome mosaic virus (BMV). The RNA in single-stranded RNA viruses may be either a plus (+) or a minus (−) strand.

Although many plant viruses have RNA genomes, organization of genetic information differs between groups (the major groupings designated as monopartite, bipartite and tripartite). The genome of most monopartite plant RNA viruses is a single-stranded molecule of (+)-sense. There are at least 11 major groups of viruses with this type of genome. Examples of this type of virus are TMV and PVX. At least six major groups of plant RNA viruses have a bipartite genome. In these, the genome usually consists of two distinct (+)-sense single-stranded RNA molecules encapsidated in separate particles. Both RNAs are required for infectivity. Cowpea mosaic virus (CPMW) is one example of a bipartite plant virus. A third major group, containing at least six major types of plant viruses, is tripartite, with three (+)-sense single-stranded RNA molecules. Each strand is separately encapsidated, and all three are required for infectivity. An example of a tripartite plant virus is alfalfa mosaic virus (AMV). Many plant viruses also have smaller subgenomic mRNAs that are synthesized to amplify a specific gene product.

DNA Plant Viruses

Plant viruses with a double-stranded DNA genome include Cauliflower Mosaic virus (CaMV).

Plant viruses with single-stranded DNA genomes include geminiviruses, and more specifically, include African Cassava Mosaic Virus (ACMV), Tomato Golden Mosaic Virus (TGMV), and Maize Streak Virus (MSV). Geminiviruses are subdivided on the basis of whether they infect monocots or dicots and whether their insect vector is a leafhopper or a whitefly. Subgroup I geminiviruses are leafhopper-transmitted and infect monocotyledonous plants (e.g., Wheat Dwarf Virus); Subgroup II geminiviruses are leafhopper-transmitted and infect dicotyledonous plants (e.g., Beet Curly Top Virus); and Subgroup III geminiviruses are whitefly-transmitted and infect dicotyledonous plants (e.g., Tomato Golden Mosaic Virus, TGMV, and African Cassava Mosaic Virus, ACMV).

Subgroup I and II geminiviruses have a single (monopartite) genome. Subgroup III geminiviruses have a bipartite genome. For example, Subgroup III geminiviruses TGMV and ACMV consist of two circular single-stranded DNA genomes, A and B, of ca. 2.8 kB each in size. DNA A and B of a given Subgroup III virus have little sequence similarity, except for an almost identical common region of about 200 bp. While both DNA A and DNA B are required for infection, only DNA A is necessary and sufficient for replication and DNA B encodes functions required for movement of the virus through the infected plant.

In both TGMV and ACMV, DNA A contains four open reading frames (ORFs) that are expressed in a bidirectional manner and arranged similarly. The ORFs are named according to their orientation relative to the common region, i.e., complementary (C) versus viral (V) in ACMV and leftward (L) or rightward (R) in TGMV. Thus, ORFs AL1, AL2, AL3, and AR1 of TGMV are homologous to AC1, AC2, AC3, and AV1, respectively, of ACMV. Three major transcripts have been identified in ACMV DNA A and these map to the AV1 and AC1 ORFs, separately and the AC2/AC3 ORFs together. There is experimental evidence for the function of these ORFs. Thus, in ACMV AC1 encodes a replication protein that is essential and sufficient for replication; AC2 is required for transactivation of the coat protein gene, AC3 encodes a protein that is not essential for replication but enhances viral DNA accumulation; and AV1 is the coat protein gene. Except for the essential viral replication protein (encoded by AC1 and AL1 in ACMV and TGMV, respectively), geminivirus replication relies on host replication and transcription machinery. Although geminiviruses are single-stranded plant DNA viruses, they replicate via double-stranded DNA intermediate by 'rolling circle replication'.

Viruses as Expression Vectors

Constructing plant viruses to introduce and express non-viral foreign genes in plants has been demonstrated (U.S. Pat. No. 4,855,237, WO 9534668). When the virus is a DNA virus, the constructions can be made to the virus itself.

Alternatively, the virus can first be cloned into a bacterial plasmid for ease in constructing the desired viral vector with the foreign DNA. If the virus is an RNA virus, the virus is generally cloned as a cDNA and inserted into a plasmid. The DNA plasmid is then used to make all of the constructions. The RNA virus is then produced by transcribing the viral sequence of the plasmid and translation of the viral genes to produce the coat protein(s) which encapsidate the viral RNA. The cDNA of RNA viral genome can be cloned behind a heterologous plant promoter. Such a chimeric gene, called an 'amplicon', can be introduced into a plant cell and used to transcribe the viral RNA that can replicate autonomously [Sablowski et al. (1995) *Proc. Natl. Acad. Sci. USA* vol 92, pp 6901–6905].

Geminiviruses have many advantages as potential plant expression vectors. These include 1) replication to high copy numbers, 2) small, well-characterized genomes, 3) assembly into nucleosomes, and 4) nuclear replication and transcription. The DNA A component of these viruses is capable of autonomous replication in plant cells in the absence of DNA B. Vectors in which the coat protein ORF has been replaced by a heterologous coding sequence have been developed and the heterologous coding sequence expressed from the coat protein promoter [Hayes et al., Stability and expression of bacterial genes in replicating geminivirus vectors in plants. *Nucleic Acids Res.* 17:2391–403 (1989); Hayes et al., Gene amplification and expression in plants by a replicating geminivirus vector. *Nature* (London) 334:179–82 (1988)].

Greater than full length copies of wild-type TGMV A and B genomes were transformed into petunia [Rogers et al., Tomato golden mosaic virus A component DNA replicates autonomously in transgenic plants. *Cell* (Cambridge, Mass.) 45:593–600 (1986)]. Replication was reported in the primary transformants and in some of the selfed progeny consistent with its mendelian inheritance, indicating that the chromosomally-integrated master copy, not the replicon, is inherited. This suggests that gametophytic and/or developing seed tissues lack the ability to support replication. The report did not demonstrate whether the virus replicated in non-germinating seed tissue. Prior art shows that geminiviruses are not seed-transmitted in nature [Goodman, R. M. (1981) Geminivirus. *J. Gen. Virol.* vol. 54, p 9–21]. Thus, there was no evidence that they can replicate in gametophytic tissue or developing seed.

Tomato Golden Mosaic Virus (TGMV) DNA A was modified by replacing its coat protein coding sequence with that of NPT II or GUS reporter genes or with that of 35S:NPT II gene and a greater than full length copy of the modified viruses were transformed into tobacco [Hayes et al., Stability and expression of bacterial genes in replicating geminivirus vectors in plants. *Nucleic Acids Res.* 17:2391–403 (1989); Hayes et al., Gene amplification and expression in plants by a replicating geminivirus vector. *Nature* (London) 334:179–82 (1988)]. Leaves of transgenic plants showed that the high levels of the reporter enzymes was gene copy number-dependent. However, replication of the vector and reporter gene expression were not reported in seed and the genetic stability of the vector in transgenic plants in subsequent generations was not reported. Use of the African Cassava Mosaic Virus (ACMV) in similar fashion has not been reported and it is not known that ACMV DNA or the replication protein(s) can be stably maintained in progeny plants and whether it can replicate in seed tissues.

In one report, a chimeric gene (in which the constitutive plant promoter, 35S, was fused to the TGMV sequence containing ORFs AL1, AL2, and AL3) was transformed into *Nicotiana benthamiana*. Different transgenic lines showed significant non-uniformity in the levels of 35S:AL1–3 gene expression as well as in their ability to complement viral replication [Hanley-Bowdoin et al., Functional expression of the leftward open reading frames of the A component of tomato golden mosaic virus in transgenic tobacco plants. *Plant Cell* 1:1057–67 (1989)]. In another report, chimeric genes (in which the constitutive plant promoter, 35S, was fused to the coding sequence of TGMV replication protein AL1) were transformed into tobacco. The expression of TGMV replication protein in the primary transformants supported the replication of a mutant genome A lacking the replication protein. [Hanley-Bowdoin et al., Expression of functional replication protein from tomato golden mosaic virus in transgenic tobacco plants. *Proc. Natl. Acad. Sci. USA.* 87:1446–50 (1990)]. However, neither publication reported on the genetic stability of the chimeric replication protein gene through subsequent generations nor its ability to support viral replication in seed tissue. In another report, chimeric genes (in which the constitutive plant promoter, 35S, was fused separately to the coding sequences of TGMV replication proteins AL1, AL2, and AL3) were transformed into tobacco [Hayes et al., Replication of tomato golden mosaic virus DNA B in transgenic plants expressing open reading frames (ORFs) of DNA A: requirement of ORF AL2 for production of single-stranded DNA. *Nucleic Acids Res.* 17:10213–22 (1989)]. The TGMV replication protein was expressed in progeny but the genetic stability of the chimeric replication protein gene through subsequent generations was not reported. Furthermore, it was not reported whether the transgenic plants will support replication in seed tissue.

In another disclosure, Rogers et al. (EP 221044) demonstrated the expression of foreign proteins in plant tissue using a modified "A" genome of the TGMV gemini virus. The foreign gene was inserted in place of the gene encoding the viral coat protein and the resulting plasmid transformed into plant tissue. Rogers et al. did not report tissue specific expression of the foreign protein and are silent as to the genetic stability of the transforming plasmid.

All of the reported viral vectors have a major disadvantage. They were either not shown to be stably maintained in transgenic plants and/or not practically useful. Thus, despite intense efforts to develop plant viral vectors and viruses, no commercially useful plant virus-based recombinant vectors have been developed that are heritable and capable of episomal replication and expression in desired tissue(s) of the transgenic host plant without the need for infection every generation. In fact, replication of plant viruses is expected to be detrimental to the growth and development of plant cells. For example, when greater than full length copy of TGMV genome A is introduced into plant cell one-tenth as many transgenic plants are obtained than when genome B is used or when control transformations are done [Rodgers et al., Tomato golden mosaic virus A component DNA replicates autonomously in transgenic plants. *Cell* (Cambridge, Mass.) 45:593–600 (1986)]. The authors suggest this may be due to expression of a gene in TGMV A DNA. Furthermore, crude extract of plants expressing tandem copies of both TGMV A and TGMV B genomes are unable to infect *Nicotiana benthamiana plants*. This is consistent with having a low virus titer. Thus, transgenic plants that do regenerate could be selected for low level expression of a toxic viral gene product and low level of viral replication or are silenced by the host. This is also consistent with the authors' finding that relatively few cells initiate release of the virus, a conclusion based on their observation that most of the tissues remain viable and nonsymptomatic. Similarly, poor replication in transgenic plants containing 35S:replication protein in other reports suggests plants are either selected for poor expression of the replication protein (presumably because of its toxicity), or that the tissue-specific expression profiles of the replication gene is different from that of viral replication.

To date, no plant virus-based recombinant vectors are known that are heritable and capable of episomal replication and expression of foreign proteins in target tissue(s) of a transgenic host plant without the need for infection in every generation.

Although, the use viral vectors for gene silencing has been reported [[Covey, S. N. et al. (1997) *Nature* (London) 385:781–782; Kumagai et al. (1995) *Proc. Natl. Acad Sci.* (U.S.A.) 92:1679–1683; Kjemtrup, S. et al. (1998) *Plant J.* 14:91–100; Ratcliff, F. et al. (1997) *Science* (Washington, D.C.) 276:1558–1560; Ruiz, M. T. et al. (1998) *Plant Cell* 10:937–946; Baulcombe, D. C. and Angell, S. M. (1998) Virus amplicons for gene silencing in transgenic plants, PCT Int. Appl. WO 9836083], its use in transgenic plants under the control of conditional or regulated site-specific recombination has not been reported thus far. In the absence of such regulation, current viral gene silencing is constitutively on. This could be detrimental to a plant and restricts transgenic viral silencing to non-essential genes. Although the use silencing suppressors genes for overcoming silencing of transgenic genes has been demonstrated, their use in preventing silencing of transgenes in viral episomes has yet not been demonstrated.

Transgenic viral vectors for foreign protein production and/or gene silencing differ from infecting viral vectors in not requiring systemic movement. Use of constitutively expressed viral transgenes genes for viral resistance has been reported. However, conditional expression of such transgenes, preferably through conditional activation of replicon, say upon viral infection, is likely to provide a more effective control.

Conditional or regulated expression has been reported in plants [see De Veylder, L. et al., *Plant Cell Physiol.* 38:568–577 (1997); Gatz, C., *Annu. Rev. Plant Physiol. Plant Mol. Biol.* 48:89–108 (1997); Hansen, G. et al., *Mol. Gen. Genet.* 254:337–343 (1997); Jepson, I., PCT Int. Appl. (1997) WO 9706269 A1; Jepson, I, et al. PCT Int. Appl. (1997) WO 9711189 A2, and other references within this application]. However, when tested for stringently for basal non-specific expression, very few have been strictly specific [Odell J. T. et al., *Plant Physiol.* 91994) 106:447–458; van der Geest et al., *Plant Physiol.* (1995), 109(4), 1151–58; Ma et al., *Aust. J Plant Physiol.* (1998), 25(1), 53–59; Czako et al., *Mol. Gen. Genet.* (1992), 235(1), 33–40]. Such promoters are not suitable for some applications, such as the use of transgenes for expressing novel phytotoxic proteins, enzymes that lead to the biosynthesis of phytotoxic products, and/or gene silencing. Site-specific recombinations in plants (Odell et al., *Plant Physiol.* 106:447–458 (1994); Odell et al., PCT Int. Appl. (1991) WO 9109957; Surin et al., PCT Int. Appl.(1997) WO 9737012) and the reduction in the proficiency of Cre-mediated recombination by mutant lox P sites and their use in increasing the frequency of Cre-lox based integration have been reported [Albert et al., *Plant J.* 7:649–59 (1995); Araki et al., *Nucleic Acids Res.* 25:868–872 (1997)]. However, the use of the mutant sites to enhance the specificity Cre-mediated recombination in conjuction with chimeric Cre genes under the control of available regulated promoters has not been demonstrated. Thus, there is a need for an appropriately stringent, site-specific recombination system for a commercially-attractive, conditional site-specific recombination.

SUMMARY OF THE INVENTION

The present invention provides a binary transgenic viral expression system comprising:
(i) a chromosomally-integrated inactive replicon comprising:
  a) cis-acting viral elements required for viral replication;
  b) a target gene comprising at least one suitable regulatory sequence; and
  c) site-specific sequences responsive to a site-specific recombinase; and
(ii) a chromosomally-integrated chimeric transactivating gene comprising a regulated plant promoter operably-linked to a site-specific recombinase coding sequence;
wherein expression of the chimeric transactivating gene in cells containing the inactive replicon results in the site-specific recombination, activation of replicon replication, and increased expression of the target gene.

The invention further provides that inactive replicon be derived from a geminivirus or a single stranded RNA virus.

Additionally the invention provides that the regulated plant promoter may be tissue-specific, constitutive or inducible and the wild-type or mutant, site-specific sequences responsive to a site-specific recombinase, the site-specific sequences may be lox sequences, responsive to the Cre recombinase protein.

The invention further provides a method of altering the levels of a protein encoded by a target gene in a plant comprising: (i) transforming a plant with the instant viral expression system of; and (ii) growing the transformed plant seed under conditions wherein the protein is expressed.

Additionally the invention provides a method of altering the levels of a protein encoded by a target gene in a plant comprising:
(i) transforming a first plant with a inactive replicon to form a first primary transformant, the inactive replicon comprising:
  a) cis-acting viral elements required for viral replication;
  b) a target gene comprising at least one suitable regulatory sequence; and
  c) site-specific sequences responsive to a site-specific recombinase,
(ii) transforming a second plant with a chimeric transactivating gene to form a second primary transformant comprising a regulated plant promoter operably-linked to a transactivating site-specific recombinase coding sequence;
(iii) growing the first and second primary transformants wherein progeny from both seeds are obtained; and
(iv) crossing the progeny of the first and second transformants wherein the target gene is expressed.

In an alternate embodiment the invention provides a method of altering the levels of a protein encoded by a target gene in a plant comprising:
(i) transforming a plant with a inactive replicon the inactive replicon comprising:
  a) cis-acting viral elements required for viral replication;
  b) a target gene comprising at least one suitable regulatory sequence; and
  c) site-specific sequences responsive to a site-specific recombinase;
(ii) infecting the transformant with a virus containing a chimeric transactivating gene comprising a regulated plant promoter operably-linked to a transactivating site-specific recombinase coding sequence;

wherein expression of the chimeric transactivating gene in cells containing the inactive replicon results in the site-specific recombination, activation of replicon replication, and increased expression of the target gene.

In another embodiment the invention provides a binary transgenic expression system comprising an inactive transgene and a chimeric transactivating gene, the inactive transgene comprising;

i) cis-acting transcription regulatory elements inoperably-linked to the coding sequence or functional RNA, and ii) site-specific sequences responsive to a site specific recombinase;

the chimeric transactivating gene comprising a regulated plant promoter operably-linked to a transactivating site-specific recombinase coding sequence, wherein expression of the chimeric transactivating gene in cells containing the inactive transgene results in an operable linkage of cis-acting transcription regulatory elements to the coding sequence or functional RNA through the site-specific recombination and increased expression of the target gene.

In an alternate embodiment the invention provides a binary transgenic expression system comprising:

(i) a chromosomally integrated blocking fragment bounded by site-specific sequences responsive to a site-specific recombinase; and (ii) a chromosomally integrated inactive silencing suppresser transgene;

wherein expression of the site specific recombinase results in the site-specific recombination that activates the silencing suppressor gene.

Additionally the invention provides a transgenic viral expression system comprising:

(i) a chromosomally-integrated geminivirus proreplicon comprising:

a) cis-acting viral elements required for viral replication;

b) a target gene comprising at least one suitable regulatory sequence; and c) flanking sequences that enable the excision of the elements of a) and b), wherein the proreplicon lacks a functional replication gene for episomal replication;

(ii) a chromosomally-integrated chimeric trans-acting replication gene comprising a regulated plant promoter operably-linked to a geminivirus viral replication protein coding sequence; and (iii) a dimer of the geminivirus B genome;

wherein expression of the trans-acting replication gene in cells containing the proreplicon results in the replication of the proreplicon and the B-genome, and increased expression of the target gene.

A further object of the invention is to provide a transgenic geminivirus expression system comprising:

(i) a chromosomally-integrated inactive replicon comprising:

a) cis-acting viral elements required for viral replication;

b) a target gene comprising at least one suitable regulatory sequence; and c) site-specific sequences responsive to a site-specific recombinase;

(ii) a chromosomally-integrated chimeric transactivating gene comprising a regulated plant promoter operably-linked to a site-specific recombinase coding sequence;

(iii) a dimer of a geminivirus B genome;

wherein expression of the chimeric transactivating gene in cells containing the inactive replicon results in the site-specific recombination, activation of replicon and B-genome replication, and increased expression of the target gene.

Yet another object of the invention is to provide a method of increasing vial resistance in a plant comprising:

(i) transforming a first plant with a inactive replicon to form a first primary transformant, the inactive replicon comprising:

a) cis-acting viral elements required for viral replication;

b) viral sequences homologous to the infecting virus capable of conferring homology-dependent resistance c) site-specific sequences responsive to a site-specific recombinase;

(ii) transforming a second plant with a chimeric transactivating gene to form a second primary transformant comprising a regulated plant promoter operably-linked to a transactivating site-specific recombinase coding sequence;

(iii) growing the first and second primary transformants wherein progeny from both seeds are obtained; and (iv) crossing the progeny of the first and second transformants wherein the viral sequences homologous to the infecting virus are expressed, conveying viral resistance to the plant.

The invention additionally provides a ternary expression system comprising: a) a first recombinase element comprising a first promoter operably linked to a sequence encoding a first recombinase; b) a second recombinase element comprising a second promoter, a stop fragment bounded by site specific sequences responsive to the first recombinase and a sequence encoding a second recombinase wherein the presence of the stop fragment inhibits the transcription or translation of the second recombinase, and wherein the first and second recombinases are different; and c) a DNA molecule bounded by site specific sequences responsive to the second recombinase; wherein expression of the first recombinase excises the stop fragment from the second recombinase element, operably linking the second promoter and the sequence encoding the second recombinase, and wherein expression of the second recombinase results in site specific recombination within the DNA molecule bounded by site specific sequences responsive to the second recombinase.

The present invention is useful in transgenic plants for controlled replicon replication and expression of transgenes with or without replicon replication. Both components of the system are chromosomally-integrated and independently heritable. One component is an inactive replicon that is unable to replicate episomally unless a transactivating protein is provided in trans. The second component is a chimeric trans-activating gene in which the coding sequence of a transactivating protein is placed under the control of a tissue- or development-specific and/or inducible promoter. The transactivating protein can be either a viral replication protein or a site-specific recombination protein. When it is a viral replication protein(s), the inactive replicon is of the proreplicon type that lacks a functional replication protein(s) and cannot replicate episomally unless the replication protein(s) is provided in trans. When it is a site-specific recombinase, it can mediate site-specific recombination involving cognate site-specific sequence(s) in the inactive replicon to convert it into an active one capable of autonomous or cis replication. The two systems involving a replicon can be used independently or in combination.

The site-specific recombination system can also be applied to transactivation of an inactive transgene with or without involving episomal replication.

The different components of the invention are heritable independently and may be introduced together into a transgenic plant or brought together by crossing transgenic plants carrying the separate components, such as by the method to produce TopCross® high oil corn seed [U.S. Pat. No. 5,704,160]. Also provided are methods of making the expression cassettes and methods of using them to produce transformed plant cells having an altered genotype and/or phenotype.

BRIEF DESCRIPTION OF FIGURES AND SEQUENCE DESCRIPTIONS

The following sequence descriptions and sequences listings attached hereto comply with the rules governing nucleotide and/or amino acid sequence disclosures in patent applications as set forth in 37 C.F.R. §1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST2.5 (1998) and the sequence listing requirements of the EPO and PCT (Rules 5.2 and 49.5(a-bis), and Section 208 and Annex C of the Administration Instructions). The Sequence Descriptions contain the one letter code for nucleotide sequence characters and the three letter codes for amino acids as defined in conformity with the IUPAC-IYUB standards described in *Nucleic Acids Res.* 13:3021–3030 (1985) and in the *Biochemical Journal* 219:345–373 (1984) which are herein incorporated by reference.

Sequences 1–42 are given in the present application, all corresponding to primers used in gene amplification.

DETAILED DESCRIPTION OF THE INVENTION

The present invention provides a binary expression system that uses various genetic elements of plant DNA or RNA viruses, regulated promoters, and/or site-specific recombination systems. The expression system is useful for conditional episomal replication, transgene expression with or without episomal replication, virus-induced host gene silencing, and viral resistance. Such replicons can be either capable or incapable of cell to-cell or systemic movement.

Applicant solved the stated problems by methods providing a two-component expression system, at least one of which is chromosomally-integrated.

Figure 1:
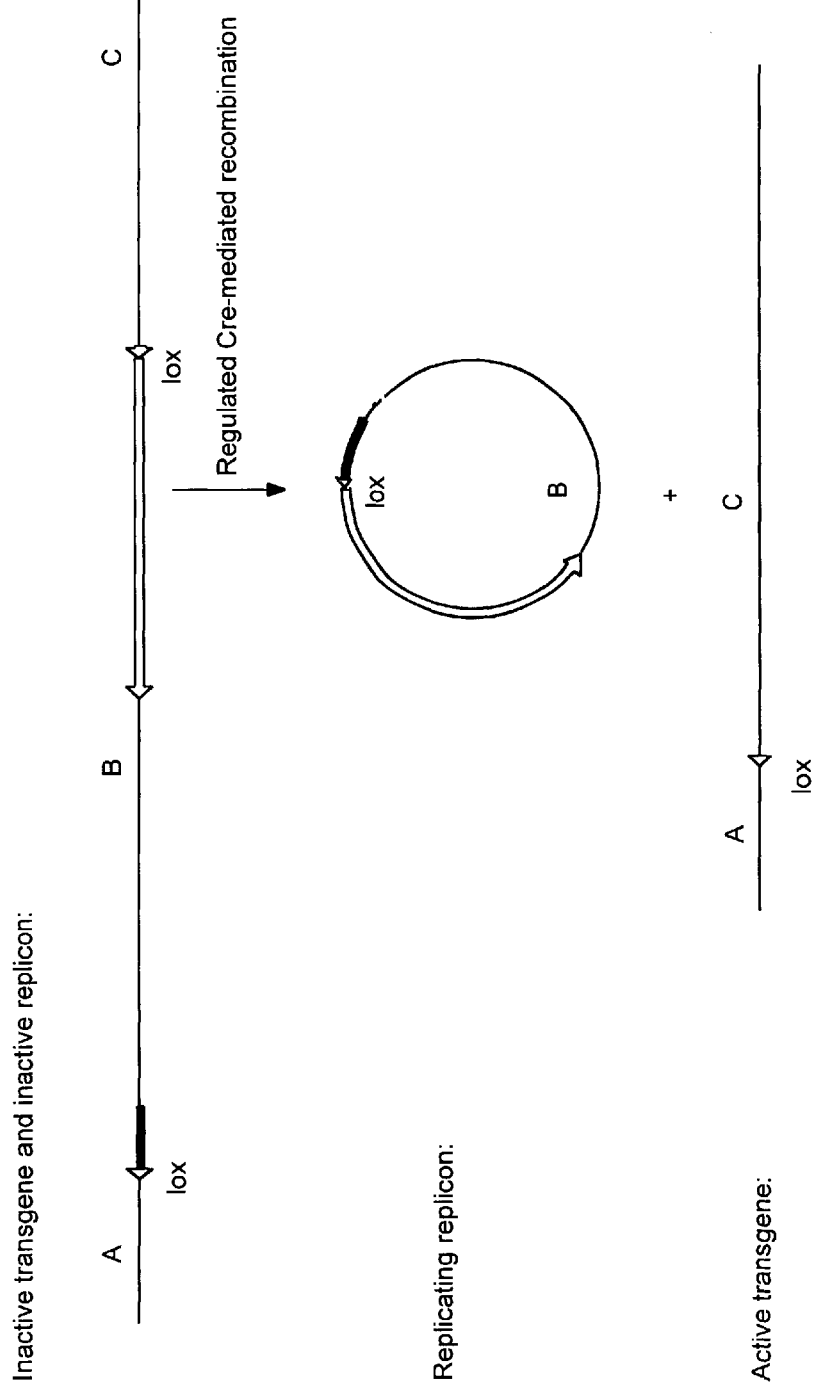
FIG. 1 illustrates excising and regulating the expression of a replicon and generating an active transgene from an inactive replicon containing site-specific sequences responsive to a site-specific recombinase.
Figure 2:
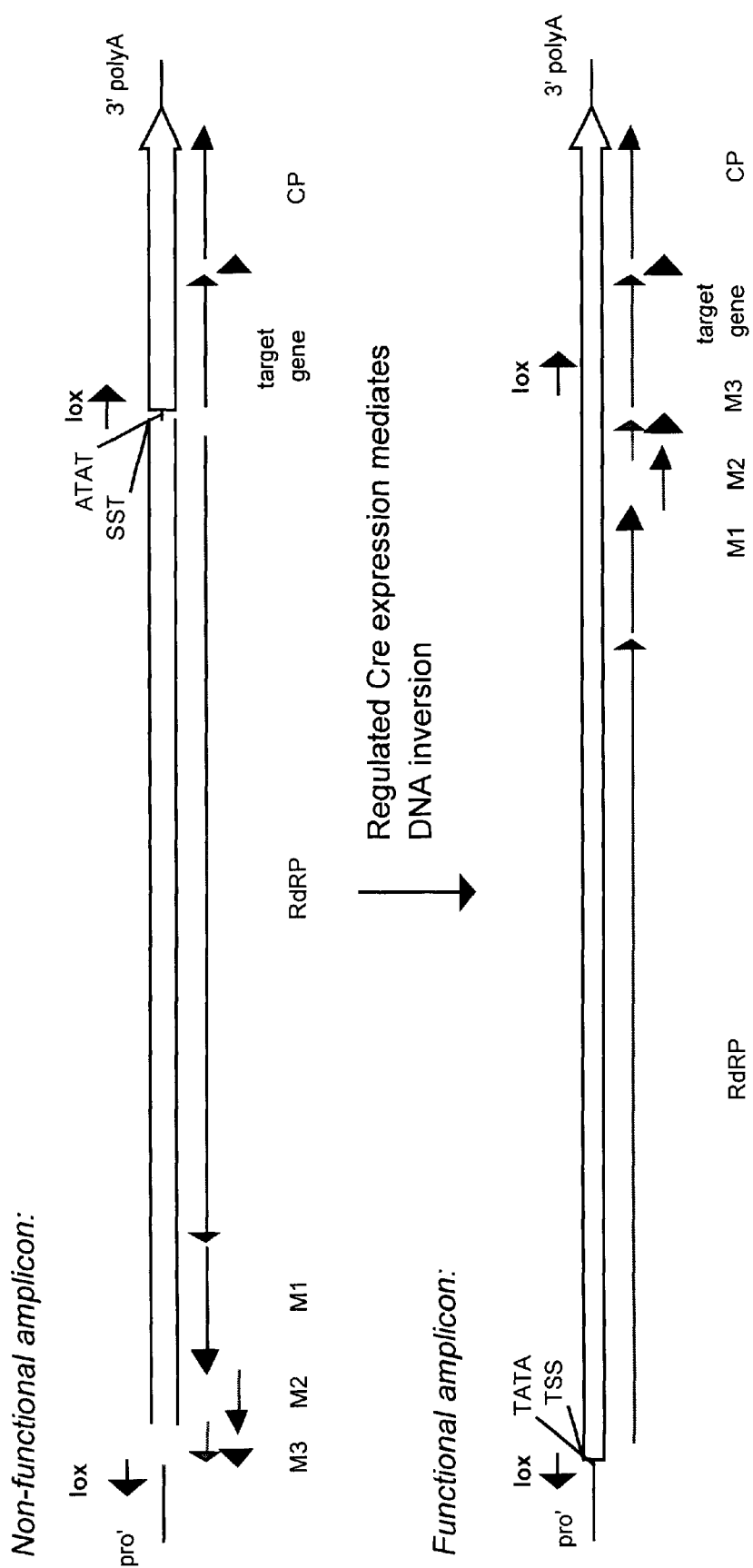
FIG. 2 illustrates excising and regulating the expression of a replicon and generating an active transgene from an inactive replicon containing site-specific sequences responsive to a site-specific recombinase where the one site-specific sequence is in the 5' non-coding transcribed sequence and the other is in an inverted orientation in the promoter.

In another method, the expression system comprises an inactive replicon and a regulated chimeric transactivating site-specific recombinase gene. The inactive replicon comprises of wild-type or mutant site-specific recombination sequences and is unable to replicate either because it cannot excise from the chromosome (in the case of DNA replicon) and/or because one or more viral genes cannot be properly transcribed (in the case of both DNA replicon and RNA virus amplicon). The transactivating site-specific recombinase mediates site-specific recombination between wild-type and/or mutant site-specific sequences in or around the inactive replicon that renders the inactive replicon active and able to replicate. Such replicons can be either capable or incapable of cell to-cell or systemic movement. Thus, the site-specific recombination mediates DNA rearrangement (excision or inversion) in the chromosome that results in either excision of a DNA replicon or RNA amplicon and/or proper transcription of one or more genes that lead to the release and autonomous (i.e., cis) replication of the replicon (FIGS. 1, 2). FIG. 1 shows a scheme for regulated transactivation of an inactive replicon or transgene by DNA excision mediated by a site-specific recombination,as for example, Cre-lox. The open triangle represents a wild type or mutant lox P site. DNA A and C can be promoter and ORF/3' untranslated region, respectively, of a transgene or they can be any DNA. DNA B can be a replicon and/or a Transcription Stop Fragment. When the construct is a geminivirus replicon inserted between the promoter (solid box) and ORF (open box) of its replication gene, the replication gene is inactive. When the replicon also serves as a Transcription Stop Fragment, its insertion inactivates the transgene and upon site-specific recombination, both replication and chromosomal transgene genes become active and the latter can be reporter for replicon excision.

Similarly, FIG. 2 is a scheme illustrating the transactivation of an inactive replicon (amplicon) by DNA inversion mediated by a site-specific recombination, as for example Cre-lox. Lox sequences are denoted by arrows above the amplicon. The open arrow denotes the replicon. The open reading frames in the replicon are denoted below the amplicon by arrows. TATA and TSS are the TATA box and the Transcription start site for the plant promoter. ATAT and SST are the TATA and TSS site, respectively, in the reverse order. M1, M2, M3 are the three movement proteins, RdRP is th RNA-dependent RNA polymerase, CP is the coat protein and the triangles are the duplicated CP promoters. Pro' and 3' poly A are regions containing the promoter and 3' polyadenylation signal.

Figure 3:
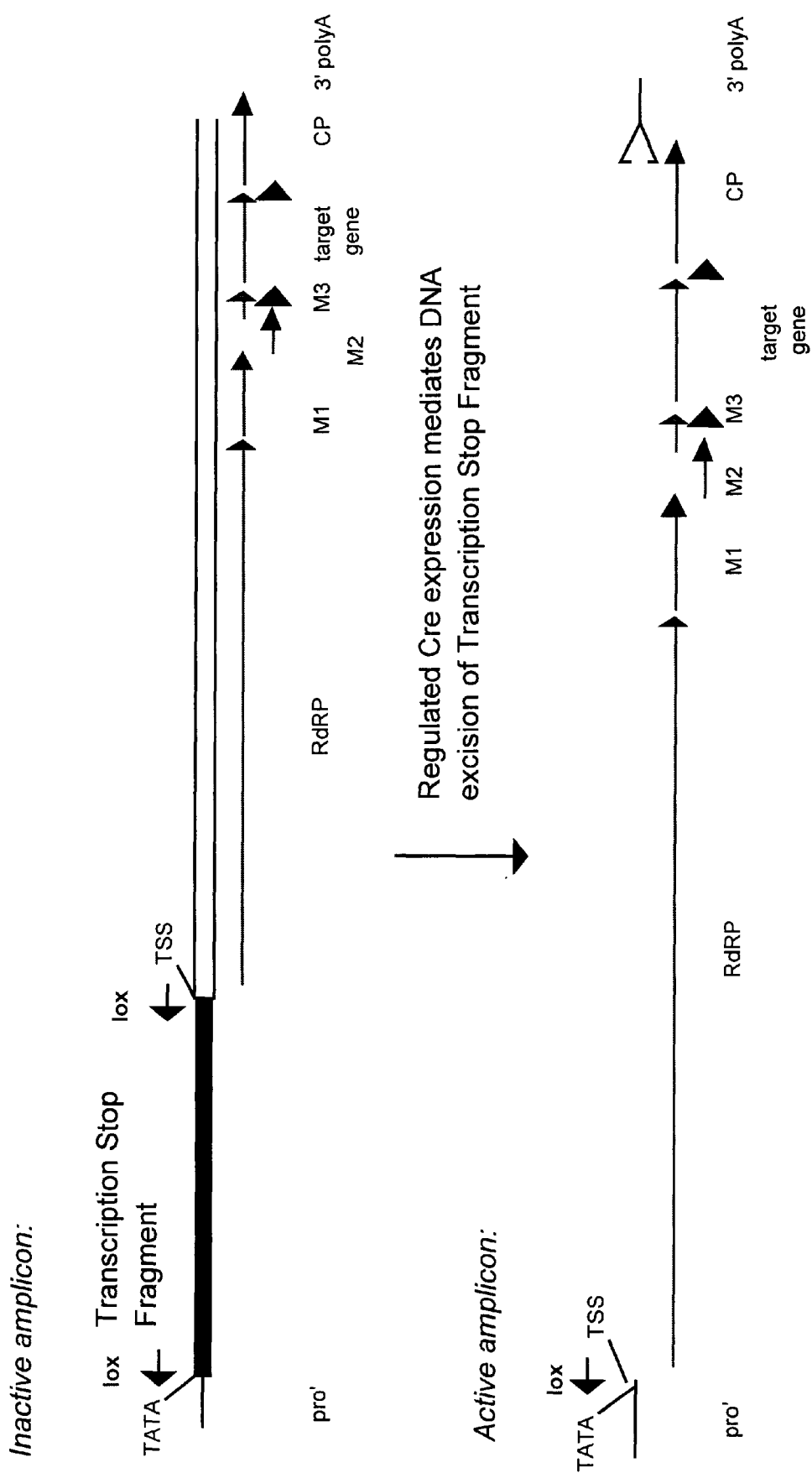
FIG. 3 illustrates excising and regulating the expression of a replicon containing a transcription stop fragment inserted between site-specific sequences where replication is mediated by a site-specific recombinase.

Alternatively, Applicant has developed a method of transactivating inactive transgenes by the above site-specific recombination system without the use of replicons (FIG. 3). FIG. 3 presents a scheme for transactivation of an inactive replicon (amplicon) by DNA excision of a Transcription Stop Fragment mediated by site-specific recombination, as for example Cre-lox. The Transcription Stop Fragment is denoted by filled box. The open arrow denotes the replicon. The open reading frames in the replicon are denoted below the amplicon by arrows. Lox sequences are denoted by arrows above the amplicon. TATA and TSS are the TATA box and the Transcription start (initiation) site for the plant promoter. M1, M2, M3, RdRP, CP is the coat protein, Pro' and 3' poly A are as described in FIG. 2.

Figure 4:
FIG. 4 illustrates excising and activating a proreplicon via the expression of a chimeric transacting replication gene.
Figure 4:
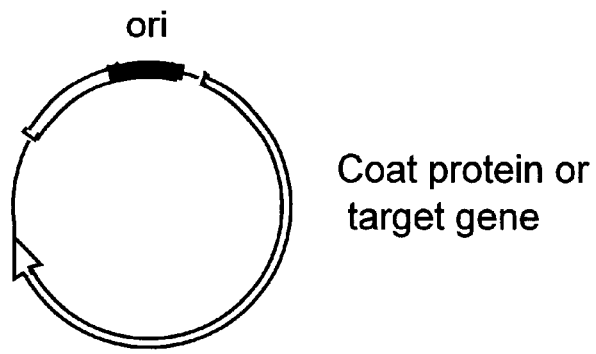

In another embodiment, the expression system comprises a proreplicon and a regulated chimeric transactivating replication gene. A proreplicon contains the cis-acting viral sequences required for replication but is incapable of episomal replication in plant cells because it lacks a functional replication gene(s) essential for replication. The transactivating gene expresses the viral replication protein missing in the 'proreplicon' and allows the proreplicon to replicate in trans (FIG. 4). Typically these viral elements are derived from geminiviruses. FIG. 4 illustrates a scheme for transactivating replication of an inactive replicon (proreplicon) in trans. Regulated expression of a chromosomally integrated chimeric replication gene will result in the replicative release and replication of the replicon from a chromosomally integrated master copy of the proreplicon. In this embodiment the proreplicon is preferably present as a partial or complete tandem dimer in T-DNA, such that a single replicon is flanked by cis-acting viral sequences necessary for viral replication, including the replication origin. These geminivirus dimers can serve as master copy from which replicons can be excised by replicative release (Bisaro, David. Recombination in geminiviruses: Mechanisms for maintaining genome size and generating genomic diversity. Homologous Recomb. Gene Silencing Plants (1994), 219–70. Editor(s): Paszkowski, Jerzy. Publisher: Kluwer, Dordrecht, Germany) in the presence of the replication protein in trans. The preferable source of proreplicon sequences is from a geminivirus (such as ACMV and TGMV) in which the essential replication gene (for example, AC1) is rendered non-functional by mutation (addition, rearrangement, or a partial or complete deletion of nucleotide sequences). The mutation can be in the non-coding sequence, such as the promoter, and/or it can be in the coding sequence of the replication protein so as to result either in one or more altered amino acids in the replication protein or in a frame shift. Preferentially, the mutation is a frameshift mutation at or close to the initiation codon of the replication protein so that not even a truncated replication protein is made. More preferably, the entire replication gene is deleted from the proreplicon such that there is no homology between the transactivating replication gene and the replicon in order to prevent virus-induced homology-based silencing of the transactivating replication gene during replicon replication. In addition, the proreplicon preferentially has most or all of the coat protein gene deleted and replaced by a restriction site for cloning target gene.

In this embodiment the other basic construct is a chimeric trans-acting replication gene consisting of a regulated plant promoter operably-linked to the coding sequence of a replication protein. For ACMV and TGMV geminiviruses, the replication proteins are encoded by the AC1 and AL1 ORFs, respectively. Preferably, AC2 and AC3 ORFs are included with the AC1 ORF in ACMV and AL2 and AL3 ORFs are included with the AL1 ORF in TGMV.

In the case of RNA virus proreplicons, the amplicon sequences flanking the inactive replicon, which include regulatory sequences, allow generation of the replicon as RNA transcripts that can replicate in trans in the presence of replication protein. These regulatory sequences can be for constitutive or regulated expression. Preferably, the promoter used in these amplicons will be a weak promoter in order to minimize virus-induced gene silencing [Ruiz et al., (1998) *Plant Cell*, Vol 19, pp 937–946]. Also included are the replication proteins of single-stranded RNA viruses (such as the RNA-dependent RNA polymerases) when they can support viral replication in trans (for example, Brome Mosaic Virus (BMV)).

Plant cells containing an inactive replicon replicate the replicon episomally only in the presence of a site-specific recombinase. Thus, regulated expression of a chimeric site-specific recombinase gene in such cells results in regulated replicon replication and target gene amplification. While the individual elements of the invention are heritable, the gene expression system may be heritable or limited to the progeny of the crosses that genetically combine the two elements. Thus in some applications the transgene or target genes expression will be restricted to progeny of the crosses, such as in the method for producing TopCross® high oil corn seed.

Using the present system, Applicant has demonstrated that (i) soybean and corn seed tissue will support gemini virus replication;

(ii) the expression system will effect the expression of foreign genes in tobacco, (iii) PVX amplicons can replicate in developing soybean seed; and (iv) both geminivirus and PVX viruses can be activated to replicate by the cre-lox recombination system. The present invention advances the art by providing plant viral vectors (a) which are maintained stably in the chromosome of transgenic plants;

(b) whose replication is controlled by the regulated expression of a site-specific recombinase; and (c) which can contain nucleic acid sequences encoding foreign proteins that may be expressed in the transgenic plant for foreign protein production or for silencing host plant genes. The present invention also advances the art by providing a method of conditional, high-level expression of transgenes using a regulated site-specific recombination system using mutant site-specific sequences and regulated expression of the site-specific recombinase.

The following terms and definitions shall be used to fully understand the specification and claims.

"Gene" refers to a nucleic acid fragment that expresses mRNA, functional RNA, or specific protein, including regulatory sequences. The term "Native gene" refers to gene as found in nature. The term "chimeric gene" refers to any gene that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature. A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism.

"Coding sequence" refers to a DNA or RNA sequence that codes for a specific amino acid sequence and excludes the non-coding sequences. The terms "open reading frame" and "ORF" refer to the amino acid sequence encoded between translation initiation and termination codons of a coding sequence. The terms "initiation codon" and "termination codon" refer to a unit of three adjacent nucleotides ('codon')

in a coding sequence that specifies initiation and chain termination, respectively, of protein synthesis (mRNA translation).

A "functional RNA" refers to an antisense RNA, ribozyme, or other RNA that is not translated.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences. As is noted above, the term "suitable regulatory sequences" is not limited to promoters, however, some suitable regulatory sequences useful in the present invention will include, but are not limited to constitutive plant promoters, plant tissue-specific promoters, plant development-specific promoters, inducible plant promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency. (Turner et al., *Molecular Biotechnology* 3:225 (1995)).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671–680, (1989).

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

"Constitutive expression" refers to expression using a constitutive or regulated promoter. "Conditional" and "regulated expression" refer to expression contolled by regulated promoter.

"Constitutive promoter" refers to promoters that direct gene expression in all tissues and at all times.

"Regulated promoter" refers to promoters that direct gene expression not constitutively but in a temporally- and/or spatially-regulated manner and include both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered; numerous examples may be found in the compilation by Okamuro et al., *Biochemistry of Plants* 15:1–82, 1989. Since in most cases the exact boundaries of regulatory sequences have not been completely defined, DNA fragments of different lengths may have identical promoter activity. Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysome-inducible systems.

"Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

"Non-specific expression" refers to constitutive expression or low level, basal ('leaky') expression in nondesired cells or tissues from a 'regulated promoter'.

"Inducible promoter" refers to those regulated promoters that can be turned on in one or more cell types by an external stimulus, such as a chemical, light, hormone, stress, or a pathogen.

"Operably-linked" refers to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences can be operably-linked to regulatory sequences in sense or antisense orientation.

"Expression" refers to the transcription and stable accumulation of sense (mRNA) or functional RNA. Expression may also refer to the production of protein.

"Altered levels" refers to the level of expression in transgenic organisms that differs from that of normal or untransformed organisms.

"Overexpression" refers to the level of expression in transgenic organisms that exceeds levels of expression in normal or untransformed organisms.

"Antisense inhibition" refers to the production of antisense RNA transcripts capable of suppressing the expression of protein from an endogenous or transgene.

"Co-suppression" and "transwitch" each refer to the production of sense RNA transcripts capable of suppressing the expression of identical or substantially similar transgene or endogenous genes (U.S. Pat. No. 5,231,020).

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes [see English, et al., (1996) *Plant Cell* 8:179–188]. Gene silencing includes virus induced gene silencing [see Teresa Ruiz et al., (1998) *Plant Cell* 10:937–946].

"Silencing suppressor" gene refers to a gene whose expression leads to counteracting gene silencing and enhanced expression of silenced genes. Silencing suppressor genes may be of plant, non-plant, or viral origin. Examples include, but are not limited to HC-Pro, P1-HC-Pro, and 2b proteins. Other examples include one or more genes in TGMV-B genome.

"Homologous to" refers to the similarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art [as described in Hames and Higgins (eds.) Nucleic Acid Hybridisation, IRL Press, Oxford, U.K.] or by the comparison of sequence similarity between two nucleic acids or proteins.

"Amplicon" refers to a chimeric gene in which the cDNA of a RNA virus is operationally-linked to plant regulatory sequences such that the primary transcript is the 'plus' strand of RNA virus.

"Binary viral expression system" describes the expression system comprised of two elements, at least one of which is chomosomally integrated. The first element is an inactive replicon that may contains a target gene whose expression is desired in a plant or plant cell. The second element is comprised of a regulated promoter operably-linked to a transactivating gene. The first element may be a proreplicon or may be an inactive replicon. The inactive replicon or proreplicon and a chimeric transactivating gene, functioning together, will effect replicon replication and expression of a target gene in a plant in a regulated manner. Both elements of the system may be chromosomally-integrated and may be inherited independently. Stimulating the regulated promoter driving the transactivating gene releases the replicon from the chromosome and its subsequent episomal replication. The release can be physical excision of the replicon from the chromosome involving site-specific recombination, a replicative release from a master chromosomal copy of a proreplicon in the presence of the replication protein, or transcriptional release from a master chromosomal copy of an amplicon.

"Binary transgenic viral replication system" refers to a replication system comprised of two chomosomally integrated elements. The first element may be a proreplicon or may be an inactive replicon which lacks a target gene encoding a foreign protein. The second element is comprised of a regulated promoter operably-linked to a site-specific recombinase gene. The inactive replicon and a chimeric site-specific recombinase gene, functioning together, will effect replicon replication in a plant in a regulated manner. Such a system is useful where replication of the virus is desired in a regulated manner but where no foreign gene expression is sought. For example, the regulated expression of virus may be useful in conferring resistance to a plant to viral infection.

"Transgene activation system" refers to the expression system comprised of an inactive transgene and a chimeric site-specific recombinase gene, functioning together, to effect transgene expression in a regulated manner. The specificty of the recombination will be determined by the specificity of regulated promoters as well as the use of wildtyp or mutant site-specific sequences. Both elements of the system can be chromosomally-integrated and inherited independently. Such site specific sequences are well known in the art, see for example the Cre-Lox system (Sauer, B., U.S. Pat. No. 4,959,317) as well as the FLP/FRT site-specific recombination system (Lyznik et al., *Nucleic Acids Res.* (1993), 21(4), 969–75).

"Target gene" refers to a gene on the replicon that expresses the desired target coding sequence, functional RNA, or protein. The target gene is not essential for replicon replication. Additionally, target genes may comprise native non-viral genes inserted into a non-native organism, or chimeric genes and will be under the control of suitable regulatory sequences. Thus, the regulatory sequences in the target gene may come from any source, including the virus. Target genes may include coding sequences that are either heterologous or homologous to the genes of a particular plant to be transformed. However, target genes do not include native viral genes. Typical target genes included but are not limited to genes encoding a structural protein, a seed storage protein, a protein that conveys herbicide resistance, and a protein that conveys insect resistance. Proteins encoded by target genes are known as "foreign proteins". The expression of a target gene in a plant will typically produce an altered plant trait.

The term "altered plant trait" means any phenotypic or genotypic change in a transgenic plant relative to the wild-type or non-transgenic plant host.

"Transcription Stop Fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation Stop Fragment" refers to nucleotide sequences that contain one or more regulatory signals, such as one or more termination codons in all three frames, capable of terminating translation. Insertion of translation stop fragment adjacent to or near the initiation codon at the 5' end of the coding sequence will result in no translation or improper translation. Excision of the translation stop fragment by site-specific recombination will leaves a site-specific sequence in the coding sequence that does not interfere with proper translation using the initiation codon.

"Stop fragment" or "Blocking fragment" refers to a DNA fragment that is flanked by site-specific sequences that can block the transcription and/or the proper translation of a coding sequence resulting in an inactive transgene. When the blocking fragment contains polyadenylation signal sequences and other sequences encoding regulatory signals capable of terminating transcription it can block the transcription of a coding sequence when placed in the 5' non-translated region, i.e., between the transcription start site and the ORF. When inserted in the coding sequence a blocking fragment can block proper translation by disrupting its open reading frame. DNA rearrangement by site-specific recombination can restore transcription and/or proper translatability. For example, excision of the blocking fragment by site-specific recombination leaves behind a site-specific sequence that allows transcription and/or proper translatability. A Transcription or Translational Stop Fragment will be considered a blocking fragment. A 'stop fragment' can also block transcription by disrupting the gene in the non-transcribed region, for example by its presence and/or orientation in promoter sequences either between the upstream promoter elements and the 'TATA' box or between the TATA box and the transcription start site.

The terms "in cis" and "in trans" refer to the presence of DNA elements, such as the viral origin of replication and the replication protein(s) gene, on the same DNA molecule or different DNA molecules, respectively.

The terms "cis-acting sequence" and "cis-acting element" refer to DNA or RNA sequence, whose function require them to be on the same molecule. An example of a cis-acting sequence on the replicon is the viral replication origin.

The terms "trans-acting sequence" and "trans-acting element" refer to DNA or RNA sequences, whose function does not require them to be on the same molecule. Examples of trans-acting sequence is the replication gene (ACI or AL1 in ACMV or TGMV geminiviruses, respectively), that can function in replication without being on the replicon.

"Cis-acting viral sequences" refers to viral sequences necessary for viral replication (such as the replication origin) and in cis orientation.

"Transactivating gene" refers to a gene encoding a transactivating protein. It can encode a viral replication protein(s) or a site-specific replicase. It can be a natural gene, for example, a viral replication gene, or a chimeric gene, for example, when plant regulatory sequences are operably-linked to the open reading frame of a site-specific recombinase or a viral replication protein.

"Transactivating genes" may be chromosomally integrated or transiently expressed.

"Episome" and "replicon" refer to a DNA or RNA virus or a vector that undergoes episomal replication in plant cells. It contains cis-acting viral sequences, such as the replication origin, necessary for replication. It may or may not contain trans-acting viral sequences necessary for replication, such as the viral replication genes (for example, the AC1 and AL1 genes in ACMV and TGMV geminiviruses, respectively). It may or may not contain a target gene for expression in the host plant.

"Inactive replicon" refers to a replication-defective replicon that contains cis-acting viral sequences, such as the replication origin, necessary for replication but is defective in replication because it lacks either a functional viral gene necessary for replication and/or the ability to be released from the chromosome due to its DNA arrangement involving site-specific recombination sequences. Consequently, an inactive replicon can replicate episomally only when it is provided with the essential replication protein in trans, as in the case of geminivirus proreplicon, or when its non-functional replication gene is rendered functional by site-specific recombination with or without release of the active replicon DNA from the chromosome. "Activation of replicon replication" refers to the process in which an inactive replicon is rendered active for episomal replication.

"Floxed replicon" refers to a replicon flanked by tandemly (i.e., directly, repeated) site-specific sequences. The replicon can be a full length copy of a DNA virus or RNA virus amplicon. The replicon is excised as DNA following site-specific recombination.

"Episomal replication" and "replicon replication" refer to replication of DNA or RNA viruses or virus-derived replicons that are not chromosomally-integrated. It requires the presence of viral replication protein(s) essential for replication, is independent of chromosomal replication, and results in the production of multiple copies of virus or replicons per host genome copy.

"Autonomous" or "cis" replication refers to replication of a replicon that contains all cis- and trans-acting sequences (such as the replication gene) required for replication.

"Replication origin" refers to a cis-acting replication sequence essential for viral or episomal replication.

"Proreplicon" refers to an inactive replicon that is comprised of cis-acting viral sequences required for replication, and flanking sequences that enable the release of the replicon from it. It is integrated into a bacterial plasmid or host plant chromosome and may contain a target gene. Proreplicon lacks a gene encoding a replication protein essential for replication. Therefore, it is unable to undergo episomal replication in the absence of the replication protein. Its replication requires both release from the integration and the presence of the essential replication gene in trans. The release from integration can be triggered in different ways. For example, the proreplicon can be present as a partial or complete tandem duplication, such that a full-length replicon sequence is flanked by virus sequences and such that the duplicated viral sequence includes the viral replication origin. Thus, in this case, the proreplicon serves as a master copy from which replicons can be excised by replicational release in the presence of replication protein(s) [Bisaro, David. Recombination in geminiviruses: Mechanisms for maintaining genome size and generating genomic diversity. Homologous Recomb. Gene Silencing Plants (1994), 219–70. Editor(s): Paszkowski, Jerzy. Publisher: Kluwer, Dordrecht, Germany]. Alternatively, the proreplicon can be excised by site-specific recombination between sequences flanking it in the presence of an appropriate site-specific recombinase (as described in site-specific recombination systems, such as Cre-lox and FLP/FRT systems, Odell et al. Use of site-specific recombination systems in plants. Homologous Recomb. Gene Silencing Plants (1994), 219–70. Editor(s): Paszkowski, Jerzy. Publisher: Kluwer, Dordrecht, Germany). In the case of RNA virus proreplicons, the amplicon sequences flanking the inactive replicon, which include regulatory sequences, allow generation of the replicon as RNA transcripts that can replicate in trans in the presence of replication protein. These regulatory sequences can be for constitutive or regulated expression.

"Viral replication protein" and "replicase" refer to the viral protein essential for viral replication. It can be provided in trans to the replicon to support its replication. Examples include viral replication proteins encoded by AC1 and AL1 genes in ACMV and TGMV geminiviruses, respectively. Some viruses have only one replication protein; others may have more than one.

"Replication gene" refers to a gene encoding a viral replication protein. In addition to the ORF of the replication protein, the replication gene may also contain other overlapping or non-overlapping ORF(s) as are found in viral sequences in nature. While not essential for replication, these additional ORFs may enhance replication and/or viral DNA accumulation. Examples of such additional ORFs are AC3 and AL3 in ACMV and TGMV geminiviruses, respectively.

"Chimeric trans-acting replication gene' refers either to a replication gene in which the coding sequence of a replication protein is under the control of a regulated plant promoter other than that in the native viral replication gene or a modified native viral replication gene, for example, in which a site-specific sequence(s) is inserted in the 5' transcribed but untranslated region. Such chimeric genes also include insertion of the known sites of replication protein binding between the promoter and the transcription start site that attenuate transcription of viral replication protein gene.

"Chromosomally-integrated" refers to the integration of a foreign gene or DNA construct into the host DNA by covalent bonds. Where genes are not "chomosomally integrated" they may be "transiently expressed". Transient expression of a gene refers to the expression of a gene that is not integrated into the host chromosome but is function independently, either as part of an autonomously replicating plasmid or expression cassette for example, or as part of another biological system such as a virus.

"Recombinase element" refers to a DNA element comprising a promoter operably linked to a gene encoding a site-specific recombinase. Recombinase elements of the present invention may optionally contain recombinase responsive sequences or blocking or stop fragments to allow for more highly regulated gene expression. Recombinase elements are particular useful in ternary expression systems of the present invention.

"Ternary expression system" refers to an expression system comprising two recombinase elements and a transgene.

The term "recombinase" refers to enzyme(s) that carry out site-specific recombination.

"Production tissue" refers to mature, harvestable tissue consisting of non-dividing, terminally-differentiated cells. It excludes young, growing tissue consisting of germline, meristematic, and not-fully-differentiated cells.

"Germline cells" refer to cells that are destined to be gametes and whose genetic material is heritable.

"Trans-activation" refers to switching on of gene expression or replicon replication by the expression of another (regulatory) gene in trans.

"Transformation" refers to the transfer of a foreign gene into the genome of a host organism. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050). The terms "transformed", "transformant" and "transgenic" refer to plants or calli that have been through the transformation process and contain a foreign gene integrated into their chromosome. The term "untransformed" refers to normal plants that have not been through the transformation process.

"Transiently transformed" refers to cells in which transgenes and foreign DNA have been introduced (for example, by such methods as agrobacterium-mediated transformation or biolistic bombardment), but not selected for stable maintenance.

"Stably transformed" refers to cells that have been selected and regenerated on a selection media following transformation.

"Transient expression" refers to expression in cells in which virus or transgene is introduced by viral infection or by such methods as agrobacterium-mediated transformation, electroporation, or biolistic bombardment, but not selected for its stable maintenance.

"Genetically stable" and "heritable" refer to chromosomally-integrated genetic elements that are stably maintained in the plant and stably inherited by progeny through successive generations.

"Primary transformant" and "T0 generation" refer to transgenic plants that are of the same genetic generation as the tissue which was initially transformed (i.e., not having gone through meiosis and fertilization since transformation).

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Wild-type" refers to the normal gene, virus, or organism found in nature without any known mutation.

"Genome" refers to the complete genetic material of an organism.

The term "dimer" when used in reference to the geminivirus B genome refers to at least one partial or complete tandem copy of the B genome. As used herein 'dimer' therefore refers to partial or complete tandem dimer of a geminivirus genome, such that a single replicon is flanked by cis-acting viral sequences, including the replication origin, necessary for viral replication. These geminivirus dimers can serve as master copies from which replicons can be excised by replicative release in the presence of the replication protein in trans (Bisaro, David, Recombination in geminiviruses: Mechanisms for maintaining genome size and generating genomic diversity. Homologous Recomb. Gene Silencing Plants (1994), 219–70. Editor(s): Paszkowski, Jerzy. Publisher: Kluwer, Dordrecht, Germany).

"TopCross® high oil corn seed method" refers to a commercial method of making hybrid corn seeds in the field, as described, for example, in U.S. Pat. No. 5,704,160.

The invention provides a two-component, expression system in transgenic plants. Both components are chromosomally-integrated and, thus, stably maintained by themselves.

In one embodiment of the invention, one component is an inactive replicon carrying site-specific sequence(s) that is unable to replicate by itself. The second component is a chimeric site-specific recombinase gene in which the coding sequence of a site-specific recombinase is operably-linked to a regulated promoter. Expressing the recombinase under appropriate stimulus will result in recombination between the cognate wild-type or mutant site-specific sequences in or around the inactive replicon which will activate release of the replicon and/replicon replication.

In yet another embodiment of the invention, one component is an inactive transgene carrying site-specific sequence (s) and the second component is a chimeric transactivating gene in which the coding sequence of a site-specific recombinase is operably-linked to a regulated promoter. Expressing the recombinase under appropriate stimulus will result in recombination between the cognate wild-type or mutant site-specific sequences in or around the inactive transgene which will activate transgene expression, without involving viral replication.

Thus, replicon replication and/or transgene expression can be targeted to specific plant cells by controlling the expression of replication protein(s) or recombinase to those cells. Plants will be most sensitive to cellular toxicity and/or the detrimental effect of replicon replication and/or the expression of the transgene or replication gene in early stages of plant growth and differentiation that involve cell division and differentiation. Thus, controlling such expression entirely or largely to non-dividing, terminally-differentiated cells will reduce the detrimental effect of replicon replication on plant growth and development. Examples of such terminally-differentiated cells are those in production tissue and include, but are not limited to, the storage cells of seed and root tissues and mature leaf cells.

This invention provides for a regulated, transgenic expression system. Since the components of this system are stably transformed, this invention solves the problem of episomal instability through cell divisions, since episomes are unstable in the absence of selection. When recombination between site-specific sequences in an inactive replicon or inactive transgene activates its replication or transgene expression, respectively, the system will be heritable unless the site-specific recombination involves DNA excision in germ line cells.

The replicon will be cell-autonomous, if the necessary viral movement protein(s) are not expressed in the cell. This is the case using only DNA A of geminiviruses or in using PVX with a mutation in a movement protein. The replicon will spread cell-to-cell systemically, if the necessary viral movement protein(s) are also expressed in the cell.

Transgenic plants with different constructs will be selected and regenerated into plants in tissue culture by methods known to one skilled in the art and referred to above. The ability of a transactivating chimeric site-specific recombinase gene to activate an inactive replicon in plant chromosome into replication via site-specific recombination will be tested following one of the following methods:

1. infecting the transgenic plants carrying the inactive replicon with viruses carrying the Cre gene,
2. crossing plants where one parent contains the correctly regulated chimeric Cre gene and the other the inactive replicon,
3. making two agrobacterium strains containing binary vectors with different plant selectable markers, one containing a chimeric Cre gene under the control of an appropriately regulated promoter and the other the inactive replicon.

The two components can be introduced into plants together by co-transformation or by sequential transformations.

Replication in transgenic plant tissue will be monitored by reporter gene expression or analysis of viral nucleic acids by Southern blot in the case of DNA viruses and by Northern blot in the case of RNA viruses.

Site-specific Recombination (SSR) for Conditional Expression of Transgenes

Use of developmentally-regulated or chemically-induced promoters for conditional transgene expression is usually limited either by their insufficient strength in the 'fully-on' stage or, more often, by their basal non-specific (i.e., 'leaky' expression) in the 'off' stage, depending on the application.

One can increase both the level and specificity of conditional expression by putting the coding sequence of the gene of interest under the control of a strong constitutive or regulated promoter for expression in the production tissue in such a manner that the gene is transcriptionally inactive unless it undergoes a site-specific recombination through the conditional expression of the cognate site-specific recombinase. Thus, conditional expression of the gene of interest is now dependent on the conditional expression of the recombinase. In this manner, determinants for high-level expression and for specificity are separated and one can then focus on the basal non-specific (i.e., 'leaky') expression of recombinase.

Since the levels of the recombinase enzyme required are not expected to be high, several 'specific' promoters can be used that may otherwise be too weak to express the gene of interest. Furthermore, since site-specific recombination depends on a threshold level of the recombinase, there may be a tolerance for leaky transcription that results in sub-threshold levels of recombinase.

Furthermore, increased 'tissue-selectivity' to available regulated promoters is provided by decreasing the efficiency of wild-type Cre-mediated recombination, raising the threshold of recombinase required by using either a mutant site for site-specific recombination and/or a mutant recombinase that are not proficient in recombination. Such mutants are well known, at least for the Cre-lox system. The applicants have shown that when using safener-inducible Cre expression to activate the expression of a transgene (35S:luciferase), the use of a mutant lox site (lox72) and a wild type lox P site in Cre-mediated activation of the transgene reduces the basal activity of the promoter compared to using both wild type lox P sites.

The non-specificity of recombinase expression can be further reduced (i.e., its expression specificity further increased) by other post-transcriptional approaches including:

1. using a chimeric recombinase gene that is poorly translated (such as having a non-ideal context sequence around the initiation codon following Kozak's rule or having additional short ORFs in the 5' untranslated region as in yeast GCN4 mRNA, or having 3' UTR sequences that makes mRNA unstable as described by Pamela Green (Department of Biochemistry, Michigan State University, East Lansing, Mich. 48824–1312, U.S.A.)
2. using a mutant recombinase that has less cellular stability (i.e., shorter half-life). Such mutants could be made by adding PEST sequences

[Sekhar et al., *Jrl. Receptor Signal Transduction Res.* 18 (2–3), 113–132 (1998)].

Once a system is developed in a given crop, it can be easily adapted for conditional expression of a variety of target trait genes with or without involvement of replicon.

Furthermore, replicon replication is expected to achieve high-level expression of target genes through gene amplification that is heritable. In addition, high-level transcription from these vectors may be used for gene silencing by antisense inhibition or co-suppression.

The invention further encompasses novel recombinant virus constructs including transfer vectors and methods for making them and using them. When used to transform a plant cell the vectors provide a transgenic plant capable of regulated, high-level expression though gene amplification. This regulated expression could be in response to a particular stimulus, such as the development stage, wounding of the plant (for example, by insect attack or pathogen), an environmental stress (such as heat or high salinity), or chemicals that induce specific promoters. Plants in which particular tissues and/or plant parts have a new or altered phenotype may be produced by the subject method.

The constructs include vectors, expression cassettes and binary plasmids depending upon the intended use of a particular construct. Two basic DNA constructs are required which may be combined in a variety of ways for transforming a plant cell and obtaining a transgenic plant. For agrobacterium-mediated transformation, the inactive replicon and chimeric replication gene may be combined in one binary plasmid or the two may be introduced into a cell on separate binary plasmids by either co-transformation or sequential transformations. Alternatively, the two constructs may be combined by crossing two transgenic lines containing one or the other construct.

The termination region used in the target gene in the inactive replicon as well as in the chimeric replication protein gene will be chosen primarily for convenience, since the termination regions appear to be relatively interchangeable. The termination region which is used may be native with the transcriptional initiation region, may be native with the DNA sequence of interest, or may be derived from another source. The termination region may be naturally occurring, or wholly or partially synthetic. Convenient termination regions are available from the Ti-plasmid of *A. tumefaciens*, such as the octopine synthase and nopaline synthase termination regions or from the genes for β-phaseolin, the chemically inducible lant gene, pIN (Hershey et al., Isolation and characterization of cDNA clones for RNA species induced by substituted benzenesulfonamides in corn. *Plant Mol. Biol.* (1991), 17(4), 679–90; U.S. Pat. No. 5,364,780).

It is contemplated that different site specific recombinase systems under the control of different promoters may be combined to enable a series of genetic switches for the regulated expression as well as removal of transgenes staggered over time during a single life cycle of the organism. Removal of transgene(s) from transgenic crops is useful for safety and protection of the environment, enhanced breeding, or for conditional transgene expression in only one generation, such as male sterility. For example, ternary expression systems, comprising two or more site specific recombination (SSR) systems may be designed to effect regulated expression and/or removal of trait gene. This coupling of conditional and tissue-specific promoters with two site-specific recombinations, such that the conditional expression of one activates the other later in the life cycle, allows their use as a series of genetic switches.

Figure 5:
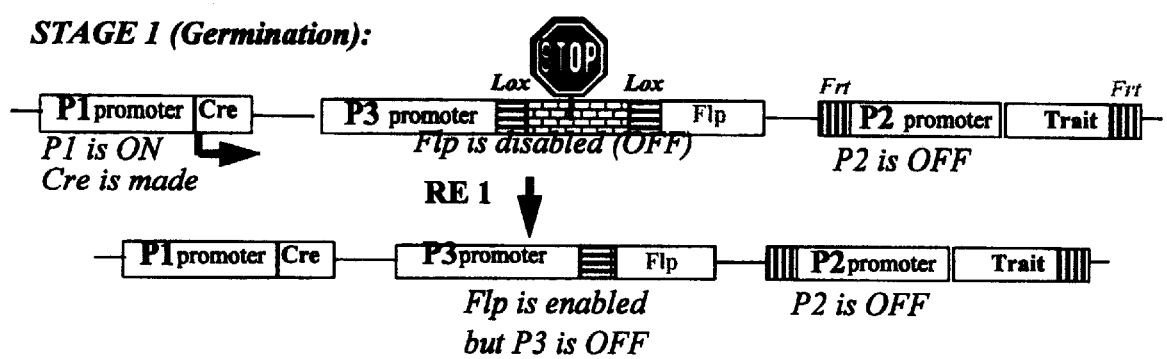
FIG. 5 illustrates the use of a ternary expression system for the regulation of trait expression where the recombinase elements are not linked to transgene expression.
Figure 5:
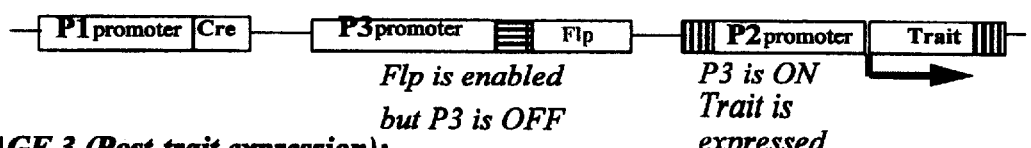
Figure 5:
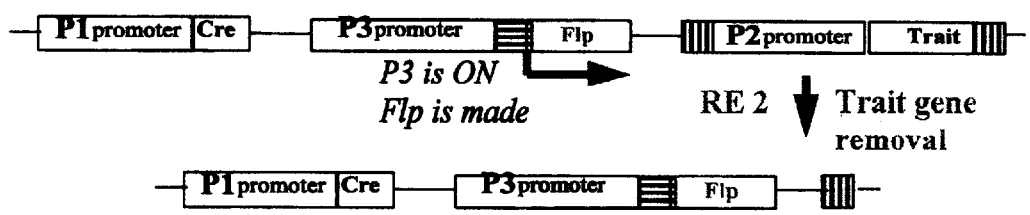

Although SSRs have been used singly as genetic switches, two (or more) SSRs under the control of different constitutive or regulated promoters can be used as a series of genetic switches within a plant's life cycle, such that conditional expression of one recombinase element (RE I) at one stage activates another recombinase element (RE II) at a later stage. Thus, one can conditionally trigger the process at a convenient developmental stage, such as germination, but get delayed effects at later stages. In one embodiment RE II may be used to remove transgenes from the genome following trait expression. For example, (referring to FIG. 5) conditional expression of Cre recombinase results in Cre-Lox RE (I) that enables (that is, removes the transcription and/or translation 'stop fragment' from it) the expression of Flp recombinase. Subsequent expression of Flp recombinase under the control of P3 promoter results in the second, Flp/Frt RE (II) that removes the trait gene leaving behind a single Frt site (FIG. 5).

Figure 6:
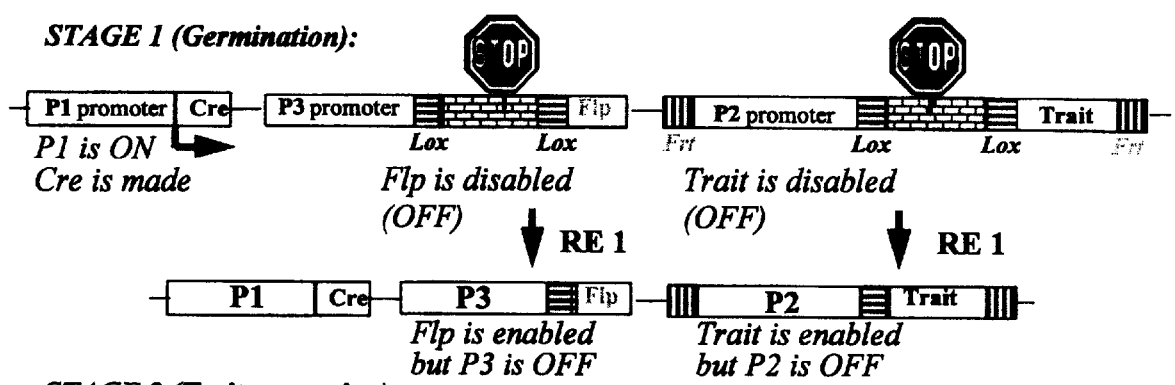
FIG. 6 illustrates the use of a ternary expression system for the regulation of trait expression where the recombinase elements are linked to transgene expression.
Figure 6:
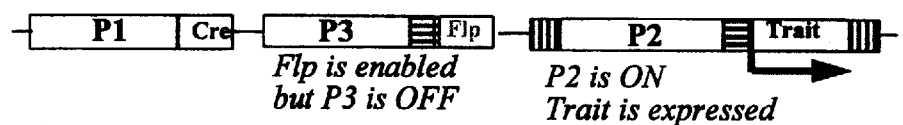
Figure 6:
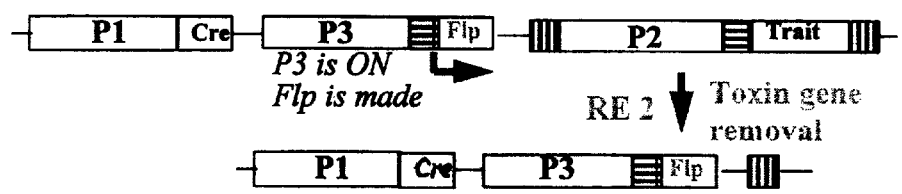

Trait gene removal may be unlinked (FIG. 5) or linked (FIG. 6) to trait gene expression. The latter provides a more stringent control of trait gene expression. Both FIGS. 5 and 6 show the trait gene being expressed in Stage 2 only, although they can be expressed in all stages (when not disabled). They also show that only the trait gene is removed, although all transgenes could be removed by having them flanked by Frt sites.

The salient feature in both schemes, is that expression of flp and/or trait genes does not have to occur immediately upon enablement (i.e., removal of the STOP fragment) by RE I but are rather controlled solely by the choices of P2 and P3 promoters, respectively. For example, RE I may occur during seed germination, whereas expression of trait and/or flp transgenes can occur at later times in development under the control of different tissue-specific promoters (e.g., seed specific promoters) with flp expression (and RE II) always following trait transgene expression in the plants life cycle as illustrated by the chart below:

| P2 (trait) promoter | Trait transgene | P3 (Flp) promoter | Pollen made | Trait in pollen | Seed made | Trait in seeds | Trait inheritance | Utility for |
|---|---|---|---|---|---|---|---|---|
| Anther-specific | Toxin | Seed-specific | No | No | Yes | Yes | No | Male sterility for hybrid seed |
| Non-seed tissue specific | Input trait | Anther-specific | Yes | No | Yes | Yes in G1 | Yes | No pollen escape of transgene |
| Non-seed tissue specific | Toxic output trait | Gametogenesis-specific | Yes | No | Yes | No | No | No trait inheritance |
| Early seed-specific | Output trait | Late seed-specific | Yes | Yes | Yes | Yes | Yes in first cycle | Seed traits in first seeds only |

Conditionality to the first SSR is provided by either chemical application or a genetic cross that combines its recombinase gene with its cognate target gene/s. The latter is more amenable for hybrid crops.

Chemical application on seeds or during germination is likely to overcome the chemical's cost and problem with its biokinetics into target cells. Chemical application can also be done in the prior generation by using a relay of three, rather than two, site-specific recombination systems. Thus, the chemical can be applied to germinating seeds in the last generation of seed production to induce one type of SSR that results in another type (RE I in above schemes), say in late seed development of progeny seeds, that, in turn, results in a third type of SSR (RE II in above schemes) to express in gametogenesis or early seeds to remove the trait gene.

In another embodiment RE I can be chemically repressible, such that the application of the chemical represses SSR I (RE I in above schemes) to allow production of seeds with the transgenic trait. Here, in the absence of the chemical, such as in the farmers' field, the crop is genetically triggered to enable trait gene expression and/or its subsequent removal on cue.

Figure 7:
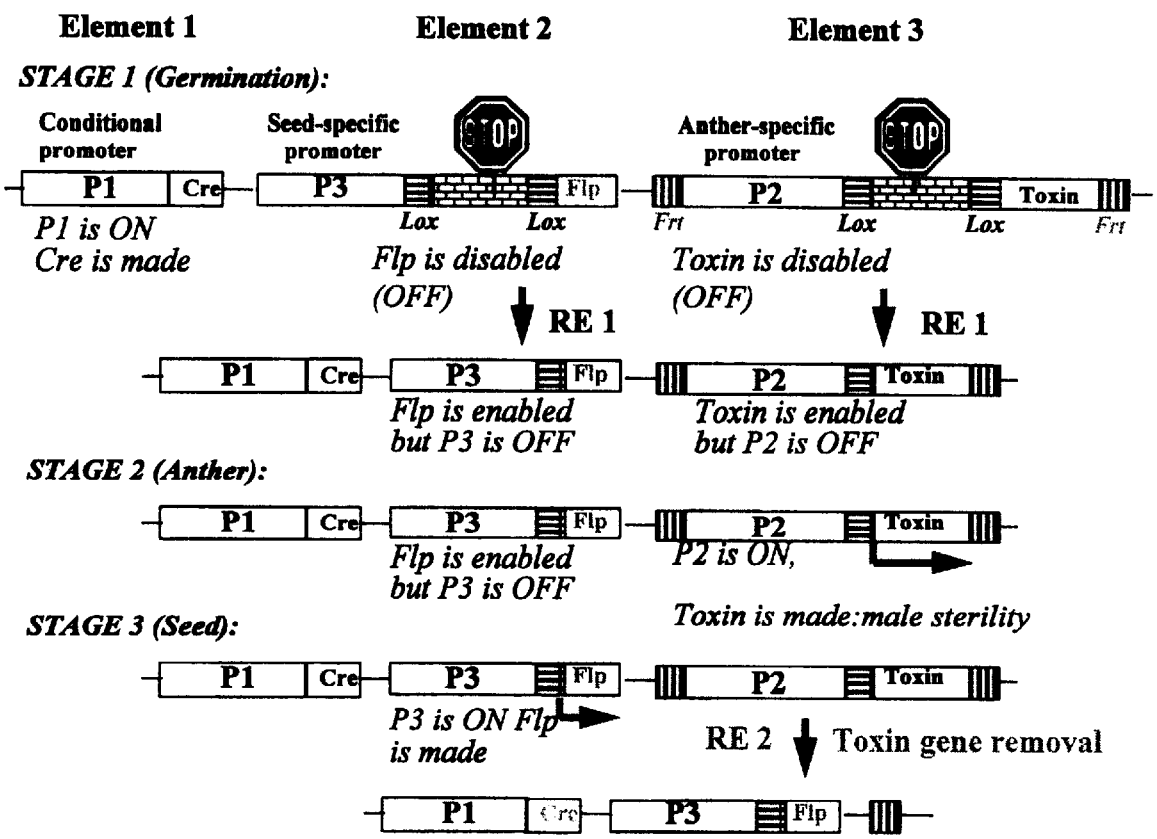
FIG. 7 illustrates the use of a linked ternary expression system for the control of pollination.

A specific application of this embodiment is illustrated in FIG. 7, which describes the use of ternary expression systems for pollination control.

For example, referring to FIG. 7, for hybrid seed production transgenic lines the following three constructs could be made:

Element 1: Promoter (P1):Cre recombinase, where P1 is a constitutive promoter or a chemically-inducible promoter, when conditionality is provided by a genetic cross or chemical application, respectively.

Element 2: Seed-specific promoter (P3):Lox:STOP:Lox: Flp recombinase.

Element 3: Frt:anther-specific promoter (P2):Lox:STOP: Lox: male sterility gene:Frt. The dominant male sterility gene can encode a toxin (e.g., barnase, avidin, RIP) gene or a co-suppressor of a fertility gene (e.g., corn MS45 gene). This element can also be a constitutive promoter expressing a co-suppressor of an anther-specific fertility gene (e.g., corn MS45 gene).

Thus, conditional Cre expression during seed germination of a plant homozygous for genetically linked Element 2 and Element 3 will enable male sterility and the subsequent Flp-mediated restoration of male fertility in the progeny, as shown in FIG. 7. When P1 is a chemically inducible promoter, conditional expression of Cre is provided by application of the chemical on the seeds or plants. When P1 is a constitutive promoter, conditional expression of Cre is provided by crossing a parent (or inbred line I) homozygous for Element 1 [constitutive promoter (P 1):Cre recombinase] with another parent (or inbred line I) homozygous for the linked Element 2 and Element 3. Such a cross can be made by conventional detasselling of the male parent or by linking the Element 1 and Elements 2/3 with different herbicide resistance genes and selecting progeny resistant to both herbicides. All F1 progeny will now be male sterile and crossing it with a male fertile line will result in male fertile F1 hybrid progeny.

When male sterility is required even in the next generation, such as in corn Top-Cross® this scheme can be modified to omit fertility restoration and incorporate a second conditional male sterility system. Thus, transgenic lines carrying the following four constructs will be made:

1. Element 1: Promoter (P1):Cre recombinase (same as above scheme for restorable male sterility).
2. Element 2: anther-specific promoter (P2):Lox:STOP: Lox: male sterility gene (same as above scheme for restorable male sterility but not flanked by Frt sites).
3. Element 3: Promoter (P1):Cre recombinase.
4. Element 4: anther-specific promoter (P2):Frt:STOP:Frt: male sterility gene (same as Element 2 in this scheme but 'stop fragment' is flanked by Frt instead of Lox sites).

Conditionality is provided by a cross between a parent (or an inbred line I) homozygous for Element 1 and Element 3 and a parent (or inbred line I) homozygous for Element 2 and Element 3. Such a cross can be made by conventional detasselling of the male parent or by linking Element 1 and Element 2 with different herbicide resistance genes and selecting progeny resistant to both herbicides. The male sterile F1 progeny of this cross (homozygous for Element 3 and heterozygous for Element 1 and Element 2) will be crossed to a parent (or inbred parent line II) homozygous for Element 4. All F1 progeny of this second cross will also be male sterile and crossing it with a male parent for Top-Cross will result in seeds with desired trait.

The Constructs

In one aspect of the invention, a novel system of trans-activating replication of plant viruses is developed using a site-specific recombination system. The system has the advantage of better tolerating non-specific basal expression (i.e., leakiness) of 'regulated' promoters and provides a more stringent control of transactivation. Furthermore, when a properly regulated site-specific recombination is developed, it can be applied generically to the activation of inactive replicons of different viruses as well as for transactivating expression of transgenes without replicon. The non-specific expression (i.e., leakiness) of some available regulated promoters expressing a site-specific recombinase (such as Cre recombinase) will be more readily tolerated by the plants since the recombinase has to reach a threshold level before it can effect recombination [(Araki et al., Targeted integration of DNA using mutant lox sites in embryonic stem cells. *Nucelic Acids Res.* 25:868–872 (1997)]). The 'specificity' of the promoters can be further increased by increasing the threshold level of the recombinase required by using either known mutant recombinase proteins, as described for Cre [Abremski K, et al., Properties of a mutant Cre protein that alters the topological linkage of recombination products. *J Mol. Biol.* 202:59–66 (1988); Wierzbicki et al., A mutational analysis of the bacteriophage P1 recombinase Cre., *J Mol. Biol.* 195:785–94 (1987) and/or mutant site-specific sequences, such as lox P sites [Albert et al., Site-specific integration of DNA into wild-type and mutant lox sites placed in the plant genome. *Plant J.* 7:659–59 (1995)], that render recombination less proficient than its wild-type site-specific recomination system and, thus, requires a higher level of the recombinase.

In this system, the inactive replicon construct contains wild-type or mutant site-specific sequences within or flanking the replicon. Recombination between the site-specific recognition sequences makes the replicon active and activates replicon replication. When the site-specific sequences are directly oriented (i.e., are in tandem), site-specific recombination will result in excision of the DNA between the site-specific sequences (FIGS. 1 and 3). When they are in an inverted orientation (i.e., in head-to-head or tail-to-tail orientation), site-specific recombination will result in inversion of the DNA between the site-specific sequences. (FIG. 2).

In another embodiment (FIG. 1), the inactive replicon construct comprises a single copy of the replicon (either a geminivirus replicon or RNA virus amplicon) flanked by tandem site-specific sequences and integrated in the chromosome. In this integrated state the replicon is inactive and unable to replicate. Site-specific recombination will excise the single copy of the replicon containing a single site-specific sequence that is capable of replication. When the replicon is inserted between the site-specific sequences at a site that is between the transcription start site and the open reading frame (i.e., in the 5' transcribed but untranslated region of the replication gene), the replication gene is non-functional and the site-specific recombination also reconstitutes the functional replication gene (FIG. 2). When the RNA amplicon is inserted between the promoter and its transcription start site, the RNA replicon is not transcribed and the site-specific recombination excises the amplicon from the chromosome as well as reconstitutes a functional aamplicon. In either case, site-specific recombination removes the replicon from the chromosome, which is preferable when avoiding virus-induced gene silencing. When the replicon is flanked by two tandem lox sites, it is refered to as a 'floxed replicon'. The floxed replicon may be integrated within a reporter gene such that it serves as a Transcription Stop Fragment and blocks proper transcription of the reporter gene. Site-specific recombination will excise the replicon and reconstitite a functional reporter gene. Such reporter gene will be useful in developing screening plants for a properly regulated Cre-lox activation system. It is preferable that a Transcription Stop Fragment is inserted near the floxed amplicon to prevent inadvertant transcription of the replication gene from sequences adjacent to the floxed amplicons, such as the context plant DNA in transgenic plants. However, it is not required that the insertion of the floxed replicon in a gene or a Transcription Stop Fragment be inserted, as long as the replication gene is not expressed in its integrated state. Inactivating the replication gene in the inactive replicon is important when its expression is detrimental to plant development.

As has been noted, gene silencing is an important obstacle in plant transgene expression and the present expression and replication systems may be modified to address this problem. Recently, pathogenicity determinants P1-HC-Pro and HC-Pro polypeptides of Tobacco Etch Virus and 2b protein of Cucumber Mosaic Virus were shown to suppress gene silencing in plants of transgenes and/or RNA virus genes [Anandalakshmi, R., Pruss, G. J., Ge, X., Marathe, R., Mallory, A. C., Smith, T. H., Vance, V. B.: A viral suppressor of gene silencing in plants. *Proc. Natl. Acad. Sci. U.S.A.* 95:13079–13084 (1998); Brigneti, G., Voinnet, O., Li, W.-X., Ji, L.-H., Ding, S.-W., Baulcombe, D. C.: Viral pathogenicity determinants are suppressers of transgene silencing in *Nicotiana benthamiana. EMBO J.* 17:6739–6746 (1998); Carrington, J. C., Whitham, S. A.: Viral invasion and host defense: strategies and counter-strategies. *Curr. Opin. Plant Biol.* 1:336–341 (1998); Vance, V. B., Pruss, G. J., Carrington, J., Martin, L., Dawson, W. O.: Potyvirus booster sequence and helper component proteinase for enhancing expression of a foreign or endogenous gene product in plants, PCT Int. Appl. WO 9844097 (1998)]. However, constitutive expression of such silencing suppressers in transgenic plants will be detrimental to plants, since it will constitutively suppress gene silencing, a fundamental plant process. This detrimental effect is especially strong in conjunction with viral vectors, since the above silencing suppressers also increase viral pathogenicity. In fact, plants infected with Potato Virus X containing HC-Pro showed severe symptoms, necrosis and stunting, while those infected with 2b protein became highly necrogenic and died in 3 weeks [Brigneti, G., Voinnet, O., Li, W.-X., Ji, L.-H., Ding, S.-W., Baulcombe, D. C.: Viral pathogenicity determinants are suppressers of transgene silencing in *Nicotiana benthamiana EMBO J.* 17:6739–6746 (1998)]. Therefore, localized and/or regulated expression of these silencing suppressers in production tissue of transgenic crops will be critically important for their practical application in increasing viral vector replication and/or for higher level gene expression, especially foreign protein production.

Applicant has observed that TGMV-B genome can also suppress virus-induced gene silencing. For example, when leaves of transgenic tobacco plants transformed with T-DNA containing floxed TGMV genome A in which the coat protein ORF was replaced with GUS ORF were co-bombarded with 35S:Cre gene and a dimer of TGMV-B genome show significantly higher expression of the GUS than those transformed with 35S:Cre gene alone. Furthermore, co-bombardment of wild type Nicotiana benthamiana with PVX-GFP and TGMV-B resulted in longer persistence of GFP activity than when bombarded with PVX-GFP alone. The applicant has discovered that infection of wild type Nicotiana benthamiana plant with TGMV carrying GFP resulted in GFP expression that did not fade or silence for at least 2 months. This infection was achieved by biolistic co-bombardment of two plasmids, collectively referred here to as 'TGMV-GFP dimers', one containing a partial dimer of TGMV-A-GFP, in which the coat protein ORF is replaced with that of brighter (mutant) form of GFP, and one containing a partial dimer of wild type TGMV-B. Furthermore, the applicant has discovered that TGMV-GFP expression was similarly persistent in plants that were silenced for PVX-GFP expression. For this, transgenic N. benthamiana plant, designated 714B-LL 1containing an inactive RNA virus PVX-GFP amplicon was used. These transgenic plants do not express any GFP because the inactive form of PVX-GFP is unable to replicate unless it undergoes Cre-lox mediated site-specific recombination. When line 714B-LL1 is bombarded with 35S:Cre gene, it results in activation of PVX-GFP replication and GFP expression that is silenced in about 2 weeks. When such a silenced 714B-LL1 plant was infected with 'TGMV-GFP dimers', GFP expression from TGMV-GFP, which is distinguishable from that in PVX-GFP by its brighter fluorescence, persisted as long as in untransformed control. Moreover, when line 714B LL-1 was co-bombarded with 35S:Cre and 'TGMV-GFP dimers', GFP expression from TGMV-GFP persisted as long as in untransformed control and beyond the time GFP from PVX-GFP was silenced. Since, the expression of a foreign gene in TGMV in the presence of TGMV-B is persistent and not silenced with time, TGMV-B may be used to enhance high level expression by suppressing silencing of transgenes present in viral vectors. It is anticipated that all geminiviruses have such silencing suppressor activity, whether with monopartite or bipartite genome. It is likely that this persistent expression of foreign gene in geminivirus results is derived from the geminivirus movement. The silencing suppressor activity of geminivirus genome B can be used in different ways. TGMV-B genome can be transformed into the host plant chromosome by one skilled in the art and combined with the cognate proreplicon or floxed genome-A. For example, TGMV-B genome can be present in its entirety as a partial dimer in the chromosome or its replication and expression may also be under the controlled activation by site-specific recombination. When present as a dimer, it may suppress silencing with or without its replication. For the former, replication may be transactivated directly by the expression of the replication protein/s under the control of a regulated promoter or indirectly by the activation of an inactive genome A via site-specific recombination. As an alternative to using the entire genome B, one could identify the silencing suppressor gene in genome B and use it to enhance foreign gene expression. Since TGMV-B has only two large ORFs, BL1 and BR1, which encode viral movement proteins, one skilled in the art can readily identify which ORF(s) is a silencing suppressor. For example leaves may be co-bombarded with 35S:Cre and TGMV-B dimer with mutant BR1 (or PVX:BL1 chimeric gene) or 35S:Cre and TGMV-B dimer with mutant BL1 (or PVX:BR1 chimeric gene) and the relative expression of GUS expression measured. The identified silencing suppressor gene may then be used for enhancing transgene expression.

Regulated expression of silencing suppresser genes can be achieved by putting them under the control of appropriately regulated promoters or, preferably, by regulated activation by site-specifc recombination. Thus, in one embodiment of the invention chimeric silencing suppressers genes will be Cre-activated. However, it would be most desirable to have the activation of both viral expression system and silencing suppresser gene expression under a common control ensuring simultaneous viral replication and suppression of gene silencing for high level viral replication and for producing high levels of foreign proteins. Thus, in another embodiment of this invention, conditional viral replication system will incorporate a conditional expression of a silencing suppresser gene. For example referring to FIG. 1, element A could be a plant promoter, such as 35S promoter, element B could be an inactive RNA virus-derived amplicon that also serves-as a transcriptional and/or translational Stop fragment of element C, and element C is the ORF of silencing suppresser gene, such PI-HC-Pro, HC-Pro, or the 2b protein (as described above) and 3' untranslated region. Regulated site-specific recombination will activate at the same time the excision and replication of the RNA viral replicon and expression of the silencing suppresser gene under the control of the promoter in element A. Similarly, referring to FIG. 1, element A could be a plant promoter, such as 35S promoter, element B could be an inactive geminivirus-derived replicon that also serves as a transcriptional and/or translational Stop fragment of element C, and element C is the ORF of silencing suppresser gene from TGMV-B genome and 3' untranslated region. Regulated site-specific recombination will activate at the same time the excision and replication of the geminivirus viral replicon and expression of the geminivirus silencing suppresser gene under the control of the promoter in element A.

Alternatively, the silencing suppresser gene can be expressed as a target gene on an inactive replicon. For example, inactive PVX amplicons with lox sites as described above (FIGS. 2 and 3) will contain in addition of the target gene of interest a silencing suppresser gene under the control of viral promoter. The target gene of interest and silencing suppresser gene in the virus replicon could be present either as tandem genes under the control of duplicated viral CP promoter or as a N- or C-terminal protein fusion with the target protein, as described by [Anandalakshmi, R., Pruss, G. J., Ge, X., Marathe, R., Mallory, A. C., Smith, T. H., Vance, V. B.: A viral suppressor of gene silencing in plants. *Proc. Natl. Acad. Sci. U. S. A.* 95:13079–13084 (1998)]. In transgenic plants, such virus-based vectors may or may not be capable of systemic spread. For example, in geminivirus-based replicons the coat protein ORF may be replaced by that of a silencing suppresser gene. Insert size limitation in replicons can be circumvented by having 2 replicons, one carrying the silencing suppresser gene and the other target gene of interest.

In another embodiment, the transcription of an essential replication gene(s) of a replicon is blocked by a Transcription Stop Fragment flanked by tandem site-specific sites and site-specific recombination excises the Transcription Stop Fragment leaving behind a single site-specific sequence that allows transcription of the previously blocked gene and subsequent replicon release and replication. For example, in TGMV and ACMV viruses, the Transcription Stop Fragment flanked by tandem site-specific sites may be inserted in the 5' transcribed but untranslated region of the replication gene, AC1 (for example, at the Mfe I site) in a viral dimer. For RNA virus amplicons, the lox site is inserted between the TATA box of the promoter and the transcription start site (FIG. 3).

In another embodiment, a region in or around a replicon is inverted by site-specific sequences to disrupt the replicon genome or the RNA virus amplicon. The inverted region can be entirely within the replicon genome resulting in disruption of the viral genome. Site-specific recombination restores the organization of the replicon, including amplicon (except for the residual site-specific sequence(s)) that allows replication. Alternatively, the inversion can be in part of the replicon and/or a plant regulatory sequence of an amplicon that disrupts proper transcription of essential replication gene(s). Site-specific recombination restores proper transcription that allows replicon release and replication.

The site-specific sequences and their cognate recombinase enzymes can be from any natural site-specific recombination systems. Well-known examples include Cre-lox, FLP/FRT, R/RS, Gin/gix systems. These are described in Odell et al., Use of site-specific recombination systems in plants. Homologous Recomb. Gene Silencing Plants (1994), 219–70. Editor(s): Paszkowski, Jerzy. Publisher: Kluwer, Dordrecht, Germany).

In one embodiment of the invention (FIG. 4), the basic inactive replicon construct is the proreplicon, which, in the case of a geminivirus replicon, is preferably present as a partial or complete tandem dimer in T-DNA, such that a single replicon is flanked by cis-acting viral sequences necessary for viral replication, including the replication origin. These geminivirus dimers can serve as master copy from which replicons can be excised by replicative release (Bisaro, David. Recombination in geminiviruses: Mechanisms for maintaining genome size and generating genomic diversity. Homologous Recomb. Gene Silencing Plants (1994), 219–70. Editor(s): Paszkowski, Jerzy. Publisher: Kluwer, Dordrecht, Germany) in the presence of the replication protein in trans. The preferable source of proreplicon sequences is from a geminivirus (such as ACMV and TGMV) in which the essential replication gene (for example, AC 1) is rendered non-functional by mutation (addition, rearrangement, or a partial or complete deletion of nucleotide sequences). The mutation can be in the non-coding sequence, such as the promoter, and/or it can be in the coding sequence of the replication protein so as to result either in one or more altered amino acids in the replication protein or in a frame shift. Preferentially, the mutation is a frameshift mutation at or close to the initiation codon of the replication protein so that not even a truncated replication protein is made. More preferably, the entire replication gene is deleted from the proreplicon such that there is no homology between the transactivating replication gene and the replicon in order to prevent virus-induced homology-based silencing of the transactivating replication gene during replicon replication. In addition, the proreplicon preferentially has most or all of the coat protein gene deleted and replaced by a restriction site for cloning target gene.

In this embodiment the other basic construct is a chimeric trans-acting replication gene consisting of a regulated plant promoter operably-linked to the coding sequence of a replication protein. For ACMV and TGMV geminiviruses, the replication proteins are encoded by the AC1 and AL1 ORFs, respectively. Preferably, AC2 and AC3 ORFs are included with the AC1 ORF in ACMV and AL2 and AL3 ORFs are included with the AL1 ORF in TGMV.

In the case of RNA virus proreplicons, the amplicon sequences flanking the inactive replicon, which include regulatory sequences, allow generation of the replicon as RNA transcripts that can replicate in trans in the presence of replication protein. These regulatory sequences can be for constitutive or regulated expression. Preferably, the promoter used in these amplicons will be a weak promoter in order to minimize virus-induced gene silencing [Ruiz et al., (1998) *Plant Cell*, Vol 19, pp 937–946]. Also included are the replication proteins of single-stranded RNA viruses (such as the RNA-dependent RNA polymerases) when they can support viral replication in trans (for example, Brome Mosaic Virus (BMV)).

Site-specific recombination can reconstitute a functional viral replicase gene and transactivate the cis replication of the replicon, which in turn can provide the replication protein in trans for the replication of the proreplicon.

The skilled person appreciates that the instant expression systems (involving inactive replicon) may be used to effect regulated replication in the absence of a target gene. In this situation foreign gene expression is not the object. Instead, regulating viral replication is sought. Such a system may be useful, for example, where regulated viral replication will confer viral resistance to the transgenic plant.

More preferably, replication of RNA virus can be transactivated by either a site-specific excision of a Transcriptional Stop fragment from the amplicon that allows normal transcription required for viral replication (FIG. 3). For example, the Transcriptional Stop fragment can be placed between the promoter and viral cDNA, within the viral cDNA, or between the viral cDNA and the 3' polyadenylation signal. Since there is limited space between the TATA box and the transcription start site, overlapping part of the lox sequence with the TATA box is preferred along with use of a deleted site-specific sequence, such as lox D117 [Abremski et al., *J Mol. Biol.* (1988) 202:59–66]. Alternatively, the replicon can be activated by site-specific inversion between two inverted site-specific sites to result in a functional amplicon (FIG. 2). These two site-specific sites can be anywhere in the amplicon as long as they do not interfere with replication following inversion. For example, one site-specific sequence can be in the 5' non-coding transcribed sequence of the GFP or GUS gene and the other in an inverted orientation between the enhancer and TATA box of the 35S promoter (FIG. 2).

When replicating replicons contain sequences homologous to chromosomal genes, the homologous gene has been reported to be silenced [Ruiz et al., (1998) *Plant Cell*, Vol. 19, pp 937–946]. When the promoter in the amplicon is expressed constitutively and strongly (such as the 35S promoter), ultimately replication can be silenced. Such silencing has been reported to confer resistance to infection by the virus. Homology-dependent virus resistance has been shown to be due to homology-dependent post-transcriptional gene silencing [see Mueller et al. (1995) The Plant Journal 7:1001–1013]. Thus, a conditional transactivation of an inactive amplicon is expected to confer resistance to infection by homologous viruses. Since such gene silencing has been reported to be dependent on mRNA threshold, when gene silencing is not desired, the promoters in the amplicon (FIGS. 2 and 3) should preferably be a weak promoter such as the minimal 35S promoter to reduce the risk of their being silenced during replicon replication.

Inactive replicons may also contain a target gene(s) that will replicate and be expressed at an enhanced level when the replicon is transactivated to replicate. The coding sequence in these target genes are operably-linked to regulatory sequences that are of viral and/or plant origin. One or more introns may be also be present in the cassette. Other sequences (including those encoding transit peptides, secretory leader sequences, or introns) may also be present in the proreplicon and replicon as desired. How to obtain and use these sequences is well-known to those skilled in the art. The target gene can encode a polypeptide of interest (for example, an enzyme), or a functional RNA, whose sequence results in antisense inhibition or co-suppression. The nucleotide sequences of this invention may be synthetic, naturally-derived, or combinations thereof. Depending upon the nature of the nucleotide sequence of interest, it may be desirable to synthesize the sequence with plant-preferred codons.

Target genes can encode functional RNAs or foreign proteins. Foreign proteins will typically encode non-viral proteins and proteins that may be foreign to plant hosts. Such foreign proteins will include, for example, enzymes for primary or secondary metabolism in plants, proteins that confer disease or herbicide resistance, commercially useful non-plant enzymes, and proteins with desired properties useful in animal feed or human food. Additionally, foreign proteins encoded by the target genes will include seed storage proteins with improved nutritional properties, such as the high-sulfur 10 kD corn seed protein or high-sulfur zein proteins.

Regulated expression of the viral replication protein(s) is possible by placing the coding sequence of the replication protein under the control of promoters that are tissue-specific, developmental-specific, or inducible.

Several tissue-specific regulated genes and/or promoters have been reported in plants. These include genes encoding the seed storage proteins (such as napin, cruciferin, .beta.-conglycinin, and phaseolin), zein or oil body proteins (such as oleosin), or genes involved in fatty acid biosynthesis (including acyl carrier protein, stearoyl-ACP desaturase, and fatty acid desaturases (fad 2- 1)), and other genes expressed during embryo development (such as Bce4, see, for example, EP 255378 and Kridl et al., *Seed Science Research* (1991) 1:209–219). Particularly useful for seed-specific expression is the pea vicilin promoter [Czako et al., *Mol. Gen. Genet.* (1992), 235(1), 33–40]. Other useful promoters for expression in mature leaves are those that are switched on at the onset of senescence, such as the SAG promoter from Arabidopsis [Gan et al., Inhibition of leaf senescence by autoregulated production of cytokinin, *Science* (Washington, D.C.) (1995), 270 (5244), 1986–8].

A class of fruit-specific promoters expressed at or during anthesis through fruit development, at least until the beginning of ripening, is discussed in U.S. Pat. No. 4,943,674, the disclosure of which is hereby incorporated by reference. cDNA clones that are preferentially expressed in cotton fiber have been isolated [John et al., Gene expression in cotton (*Gossypium hirsutum L.*) fiber: cloning of the mRNAs, *Proc. Natl. Acad. Sci. U.S.A.* (1992), 89 (13), 5769–73]. cDNA clones from tomato displaying differential expression during fruit development have been isolated and characterized [Mansson et al., *Mol. Gen. Genet.* (1985) 200:356–361; Slater et al., *Plant Mol. Biol.* (1985) 5:137–147]. The promoter for polygalacturonase gene is active in fruit ripening. The polygalacturonase gene is described in U.S. Pat. No. 4,535,060 (issued Aug. 13, 1985), U.S. Pat. No. 4,769, 061 (issued Sep. 6, 1988), U.S. Pat. No. 4,801,590 (issued Jan. 31, 1989) and U.S. Pat. No. 5,107,065 (issued Apr. 21, 1992), which disclosures are incorporated herein by reference.

Mature plastid mRNA for psbA (one of the components of photosystem II) reaches its highest level late in fruit development, in contrast to plastid mRNAS for other components of photosystem I and II which decline to nondetectable levels in chromoplasts after the onset of ripening [Piechulla et al., *Plant Mol. Biol.* (1986) 7:367–376]. Recently, cDNA clones representing genes apparently involved in tomato pollen [McCormnick et al., *Tomato Biotechnology* (1987) Alan R. Liss, Inc., New York) and pistil (Gasser et al., *Plant Cell* (1989), 1:15–24] interactions have also been isolated and characterized.

Other examples of tissue-specific promoters include those that direct expression in leaf cells following damage to the leaf (for example, from chewing insects), in tubers (for example, patatin gene promoter), and in fiber cells (an example of a developmentally-regulated fiber cell protein is E6 [John et al., Gene expression in cotton (*Gossypium hirsulum L.*) fiber: cloning of the mRNAs, *Proc. Natl. Acad. Sci. U.S.A* (1992), 89(13), 5769–73]). The E6 gene is most active in fiber, although low levels of transcripts are found in leaf, ovule and flower.

The tissue-specificity of some "tissue-specific" promoters may not be absolute and may be tested by one skilled in the art using the diphtheria toxin sequence. One can also achieve tissue-specific expression with "leaky" expression by a combination of different tissue-specific promoters (Beals et al., (1997) Plant Cell, vol 9, 1527–1545). Other tissue-specific promoters can be isolated by one skilled in the art (see U.S. Pat. No. 5,589,379). Several inducible promoters ("gene switches") have been reported. Many are described in the review by Gatz [Current Opinion in Biotechnology, 1996, vol. 7, 168–172; Gatz, C. Chemical control of gene expression, Annu. Rev. Plant Physiol Plant Mol. Biol. (1997), 48, 89–108]. These include tetracycline repressor system, Lac repressor system, copper-inducible systems, salicylate-inducible systems (such as the PR1 a system), glucocorticoid- [Aoyama T. et al., N-H Plant Journal (1997) vol 11:605–612] and ecdysome-inducible systems. Also, included are the benzene sulphonamide- (U.S. Pat. No. 5,364,780) and alcohol- (WO 97/06269 and WO 97/06268) inducible systems and glutathione S-transferase promoters. Other studies have focused on genes inducibly regulated in response to environmental stress or stimuli such as increased salinity, drought, pathogen, and wounding. [Graham et al., J Biol. Chem. (1985) 260:6555–6560; Graham et al., J Biol. Chem. (1985) 260:6561–6554] [Smith et al., Planta (1986) 168:94–100]. Accumulation of a metallocarboxypeptidase-inhibitor protein has been reported in leaves of wounded potato plants [Graham et al., Biochem Biophys Res Comm (1981) 101:1164–1170]. Other plant genes have been reported to be induced methyl jasmonate, elicitors, heat-shock, anerobic stress, or herbicide safeners.

Regulated expression of the chimeric transacting viral replication protein can be further regulated by other genetic strategies. For example, Cre-mediated gene activation as described by Odell et al. [(1990) Mol. Gen. Genet. 113:369–278]. Thus, a DNA fragment containing 3' regulatory sequence bound by lox sites between the promoter and the replication protein coding sequence that blocks the expression of a chimeric replication gene from the promoter can be removed by Cre-mediated excision and result in the expression of the trans-acting replication gene. In this case, the chimeric Cre gene, the chimeric trans-acting replication gene, or both can be under the control of tissue- and developmental-specific or inducible promoters. An alternate genetic strategy is the use of tRNA suppressor gene. For example, the regulated expression of a tRNA suppressor gene can conditionally control expression of a trans-acting replication protein coding sequence containing an appropriate termination codon as described by Ulmasov et al. [(1997) Plant Molecular Biology, vol 35, pp 417–424]. Again, either the chimeric tRNA suppressor gene, the chimeric transacting replication gene, or both can be under the control of tissue- and developmental-specific or inducible promoters.

One skilled in the art recognizes that the expression level and regulation of a transgene in a plant can vary significantly from line to line. Thus, one has to test several lines to find one with the desired expression level and regulation. Once a line is identified with the desired regulation specificity of a chimeric Cre transgene, it can be crossed with lines carrying different inactive replicons or inactive transgene for activation.

A variety of techniques are available and known to those skilled in the art for introduction of constructs into a plant cell host. These techniques include transformation with DNA employing A. tumefaciens or A. rhizogenes as the transforming agent, electroporation, particle acceleration, etc. [See for example, EP 295959 and EP 138341]. It is particularly preferred to use the binary type vectors of Ti and Ri plasmids of Agrobacterium spp. Ti-derived vectors transform a wide variety of higher plants, including monocotyledonous and dicotyledonous plants, such as soybean, cotton, rape, tobacco, and rice [Pacciotti et al. (1985) Bio/Technology 3:241; Byrne et al. (1987) Plant Cell, Tissue and Organ Culture 8:3; Sukhapinda et al. (1987) Plant Mol. Biol. 8:209–216; Lorz et al. (1985) Mol. Gen. Genet. 199:178; Potrykus (1985) Mol. Gen. Genet. 199:183; Park et al., J. Plant Biol. (1995), 38(4), 365–71; Hiei et al., Plant J. (1994), 6:271–282]. The use of T-DNA to transform plant cells has received extensive study and is amply described [EP 120516; Hoekema, In: The Binary Plant Vector System Offset-drukkerij Kanters B. V.; Alblasserdam (1985), Chapter V, Knauf, et al., Genetic Analysis of Host Range Expression by Agrobacterium In: Molecular Genetics of the Bacteria-Plant Interaction, Puhler, A. ed., Springer-Verlag, New York, 1983, p. 245; and An, et al., EMBO J. (1985) 4:277–284]. For introduction into plants, the chimeric genes of the invention can be inserted into binary vectors as described in the examples.

Other transformation methods are available to those skilled in the art, such as direct uptake of foreign DNA constructs [see EP 295959], techniques of electroporation [see Fromm et al. (1986) Nature (London) 319:791] or high-velocity ballistic bombardment with metal particles coated with the nucleic acid constructs [see Kline et al. (1987) Nature (London) 327:70, and see U.S. Pat. No. 4,945,050]. Once transformed, the cells can be regenerated by those skilled in the art. Of particular relevance are the recently described methods to transform foreign genes into commercially important crops, such as rapeseed [see De Block et al. (1989) Plant Physiol. 91:694–701], sunflower [Everett et al. (1987) Bio/Technology 5:1201], soybean [McCabe et al. (1988) Bio/Technology 6:923; Hinchee et al. (1988) Bio/Technology 6:915; Chee et al. (1989) Plant Physiol. 91:1212–1218; Christou et al. (1989) Proc. Natl. Acad. Sci USA 86:7500–7504; EP 301749], rice [Hiei et al., Plant J. (1994), 6:271–282], and corn [Gordon-Kamnm et al. (1990) Plant Cell 2:603–618; Fromm et al. (1990) Biotechnology 8:833–839].

Transgenic plant cells are then placed in an appropriate selective medium for selection of transgenic cells which are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic such as kanamycin, G418, bleomycin, hygromycin, chloramphenicol, herbicide, or the like). The particular marker used will allow for selection of transformed cells as compared to cells lacking the DNA which has been introduced. Components of DNA constructs including transcription cassettes of this invention may be prepared from sequences which are native (endogenous) or foreign (exogenous) to the host. By "foreign" it is meant that the sequence is not found in the wild-type host into which the construct is introduced. Heterologous constructs will contain at least one region which is not native to the gene from which the transcription-initiation-region is derived.

To confirm the presence of the transgenes in transgenic cells and plants, a Southern blot analysis can be performed using methods known to those skilled in the art. Replicons can be detected and quantitated by Southern blot, since they can be readily distinguished from proreplicon sequences by the use of appropriate restriction enzymes. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

The present viral expression system has been used to demonstrate that (i) soybean and corn seed tissue will support geminivirus replication; (ii) Cre can mediate site-specific recombination in transgenic inactive replicons and inactive transgenes and that this recombination leads to high foreign protein expression and/or host gene silencing, and (iii) that the expression system will effect expression of foreign genes in tobacco.

EXAMPLES

The present invention is further defined in the following Examples. These Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and Enquist, L. W. Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Restriction enzyme digestions, phosphorylations, ligations and transformations were done as described in Sambrook, J. et al., supra. Restriction enzymes were obtained from New England Biolabs (Boston, Mass.), GIBCO/BRL (Gaithersburg, Md.), or Promega (Madison, Wiss.). Taq polymerase was obtained from Perkin Elmer (Branchburg, N.J.). Growth media was obtained from GIBCO/BRL (Gaithersburg, Md.).

The *Agrobacterium tumefaciens* strain LBA4404 was obtained from Dr. R. Schilperoot, Leiden [Hoekema et al. *Nature* 303:179–180, (1983)].

Transformation Protocols

Biolistic transformations were done essentially as described in U.S. Pat. No. 4,945,050, hereby incorporated by reference. Briefly, gold particles (1 mm in diameter) are coated with DNA using the following technique. Ten ug of plasmid DNAs are added to 50 mL of a suspension of gold particles (60 mg per mL). Calcium chloride (50 uL of a 2.5 M solution) and spermidine free base (20 mL of a 1.0 M solution) are added to the particles. The suspension is vortexed during the addition of these solutions. After 10 min, the tubes are briefly centrifuged (5 sec at 15,000 rpm) and the supernatant removed. The particles are resuspended in 200 mL of absolute ethanol, centrifuged again and the supernatant removed. The ethanol rinse is performed again and the particles resuspended in a final volume of 30 uL of ethanol. An aliquot (5 mL) of the DNA-coated gold particles can be placed in the center of a flying disc (Bio-Rad Labs, 861 Ridgeview Dr, Medina, Ohio.). The particles are then accelerated into the corn tissue with a PDS-1000/He (Bio-Rad Labs, 861 Ridgeview Dr., Medina, Ohio.), using a helium pressure of 1000 psi, a gap distance of 0.5 cm and a flying distance of 1.0 cm.

Where Agrobacterium transformations were done the proceedure was accomplished essentially as described Park et al., *J. Plant Biol.* (1995), 38(4), 365–71.

Example 1

Construction of Floxed ACMV and TGMV Monomers pMHP35 was made by cloning Xba I fragment from 35SCabb:Ata (Arab ALS) into Xba I site of pTZ18R.

Introduction of the Wild-type Lox P Site between the Xho I and Sac I Sites of 35S Promoter Two tandem (i.e., directly repeated) wild-type lox P sites were introduced between the Xho I and Sac I sites in the 5' transcribed, but untranslated, region of 35S promoter: GUS:3' nos chimeric reporter gene such that the two lox P sites were separated by an Eco RI site. For this, a Xho I-Eco RI adaptor A [made by annealing primer pairs GV 48 (SEQ ID No: 1) and GV 49 (SEQ ID No:2)] and an Eco RI-Sac I adaptor B [made by annealing primer pairs GV 50 (SEQ ID No:3) and GV 51 (SEQ ID No:4)] were co-ligated into Xho I and Sac I digested plasmid carrying the 35S promoter: GUS:3' nos chimeric reporter gene.

[SEQ ID No. 1]5'-TCG AGA TAA CTT CGT ATA ATG TAT GCT ATA CGAAGT TAT G-3' (GV48)

[SEQ ID No. 2]5'-AAT TCA TAA CTT CGT ATA GCA TAC ATT ATA CGA AGT TAT C-3' (GV48)

[SEQ ID No. 3]5'-AAT TCT ATA ACT TCG TAT AAT GTA TGC TAT ACG AAG TTA TGA GCT-3' (GV50)

[SEQ ID No. 4]5'-CAT AAC TTC GTA TAG CAT ACA TTA TAC GAA GTT ATA G-3' (GV51)

The resulting plasmid was designated pGV686 and the introduced lox sites were confirmed by sequence analysis. Subsequently, the poly A signal region from nopaline synthase (3' nos) [Genbank Accession Nos. J01541 V00087] was replaced by that from octopine synthase (3' ocs) [Genbank Accession Nos. V00088 and J01820] to yield plasmid pGV690.

Insertion of TGMV and ACMV Monomer between the Lox Sites in pGV690

A single copy of a modified ACMV (in which most of the coat protein gene is deleted) was isolated as a Mfe I fragment from plasmid pGV596 (WO 99/22003) and cloned into the EcoR I site of pGV690 to yield pGV691, such that the viral origin is adjacent to the 35S promoter.

The ability of Cre to transactivate both GUS expression and viral replication was first tested by co-bombardment of floxed viral genomes, pGV691, with plasmid pNY102 containing 35S:Cre chimeric gene into leaves of *Nicotiana tabacum* var *Xanthi* and *N. benthamiana*, as well as bombarding leaves of Xanthi plants stably transformed with 35S:Cre gene. Gus activity and replicon replication were detected only in the presence of Cre, providing evidence that Gus is a good reporter for excision, that geminivirus replication can tolerate at least one lox site, and that the expression of Cre from a chromosomally integrated chimeric Cre gene can transactivate viral replication. When pGV691, pGV596d (a ACMV proreplicon with a mutant replication protein described in PCT Int. Appl WO 99/22003), and pNY102 were co-bombarded, trans replication of proreplicon from pGV596d as well as cis replication of replicon from pGV691 was observed.

The Pvu II site in pGV691 was converted into Xma I using NEB 1048 Sma I linker and then the Xma I-H3 fragment was cloned into pSK (Stratagene, 11011 North Torrey Pines Road La Jolla, Calif. 92037), Xma I-Hind III to yield pGV696. pGV699 was made by cloning a Pst I fragment from pGV697 containing a Transcriptional Stop fragment consisting of tandem 3' untranslated regions of small subunit of ribulose-1,5-bisphosphate carboxylase and nopaline synthase genes into the Pst I site of pGV696 in the desired orientation to prevent inadvertant transcription of the viral replicase gene by a plant promoter within T-DNA or adjacent to its insertion site. The Xma I-Hind III fragment from pGV699 was cloned into pBE673, a binary vector for bar selection (described in PCT Int. Appl WO 99/22003) to yield pBE704. To make a binary vector containing both floxed ACMV vector and a dimer of a replication-defective mutant of ACMV, the Sac I-Xma I fragment of pGV596d containing the mutant ACMV dimer was cloned into Sac I-Xma I pBE673 binary vector to make pBE695. Next the Xma I-H3 fragment of pGV699 was cloned into pBE695 to form pBE705. pBE704 and pBE705 constructs were introduced into N. benthamiana and N. tabacum through agrobacterium-mediated transformation as described above either alone or in the presence of ACMV proreplicon pGV596d. Bombardment of transgenic plants with Cre showed activation of GUS expression and replication of ACMV replicon was observed in both 704 and 705 transformants. In addition, replication of the mutant ACMV replicon was observed in 705 transformants confirming the data from transient analysis. Results indicated that replication of excised replicon was significantly higher in the absence than the presence of the proreplicon.

The GUS ORF in pGV690 was replaced with one carrying the Luc ORF from pSP-luc+vector from Promega (2800 Woods Hollow Road Madison, Wis. 53711) using Nco I-Xba I to make pGV716. A single copy full-length genome of TGMV was isolated as a 2.6 kb Mfe I fragment from plasmid pTA1.3 (N. Robertson, North carolina State University) was cloned into the Eco RI site between Lox P sites of pGV716 to result in 'floxed' TGMV replicons in plasmid pGV731, such that the viral origin is adjacent to the 35S promoter. The coat protein gene in pGV731 was replaced with the GUS ORF from pGV671 (PCT Int. Appl. WO 99/22003) using NdeI/SalI to yield pGV733. Bgl II to Hind III fragment of pGV733 was cloned into Bam HI/Hind III cut pBE673 to yiled pBE733, a bar binary vector.

A binary vector pBE736 was made that was identical to that in pBE733 except that one of the lox sites was changed from wild type P to mutant lox 72 [Albert et al., Plant J. 7:649–59 (1995)]. The floxed replicons with mutant lox sites was introduced into a binary vector and the modified binary vectors were introduced into *agrobacterium tumefaciens* and transformed into plants by agrobacterium-mediated transformation. Progeny of the plants were collected and will be crossed with lines containing correctly-regulated Cre gene.

The binary vectors pBE733 and pBE736 were transformed into agrobacterium and introduced into tobacco (*Nicotiana tabacum* var. *Xanthi*) and *Nicotiana benthamiana* leaf discs by agrobacterium-mediated transformation (using 25 mls of the agro' culture at OD A600 of 1.0). After 3 days on MS media the disks were incubated for 6 weeks on shooting medium (MS media supplemented with 1 mg/ml claforan 1 ug/mi BAP, 0.1 ug/ml NAA) containing 10 and 6 ug/ml PPT (Sigma Chemical Co., 6050 Spruce St., St. Louis, Mo. 63103) for tobacco and benthamiana, respectively. BE733 transformants were confirmed for transgene by Southern analysis and analysed for replication by Southern and for GUS expression upon bombardment of a plasmid pNY102 containing 35S:Cre gene.

Transgenic tobacco and N. benthamiana containing the floxed TGMV from pBE733 were obtained. Bombardment of transgenic leaf or plant with PVX:Cre and 35S:Cre gave distinct GUS staining expected for replication. T1 progeny seedlings of N. benthamiana line 733 # 23, was infected with PVX-Cre. This resulted in GUS expression in infected leaves that persisted for upto 25 days with no apparent silencing. These results confirmed that the inactive replicon was heritable and capable of being activated by Cre-mediated excision.

Example 2

Inactive PVX-GFP and PVX-GUS Amplicons with Lox Sites

Plasmids pVX201, pTXS-GFP, and TXGC3S.vec were obtained from Dr. D. Baulcombe (The Sainsbury Laboratory, John Innes Centre, Norwich Research Park, Norwich Research Park, NR4 7UH, UK). pVX201 contains a clone of 35S:PVXcDNA:3' nos ('PVX amplicon'), pTXS-GFP contains T7 promoter:PVX-GFP construct, and TXGC3S.vec contains T7 promoter:PVX-GFP construct. The GFP and GUS ORFs were cloned behind the PVX coat protein promoter.

pGV680, containing PVX-GFP ('PVX-GFP amplicon'), was made by replacing the Sac I-Avr II fragment of pVX201 amplicon with that from pTXS-GFP containing the GFP ORF. pGV681, containing the PVX-GUS ('PVX-GFP amplicon'), was made by replacing the Sac I-Avr II fragment of pVX201 amplicon with that of TXGC3S.vec containing the GUS ORF. A frameshift mutation in the open reading frame of the viral RNA-dependent RNA polymerase of pGV680 and pGV681 yielded plasmids pGV682 and pGV683, respectively. This mutation was made by restricting pGV680 and pGV681 DNAs with Age I, filling-in, and religation.

Detached leaves of *Nicotiana benthamiana* were bombarded with the above plasmids using the biolistic gun. Analysis of leaves 10–14 days after bombardment showed that GFP fluorescence was detected in leaves bombarded with pGV680 but not pGV682 and that GUS staining was detected in leaves bombarded with pGV681 but not pGV683. This confirmed that the reporter gene expression was dependent on a functional viral RNA-directed RNA polymerase (RdRP) and that reporter genes can be used to detect replication.

When pGV681 was bombarded into cotyledons ca. 50–100 mg soybean zygotic embryos, GUS staining detected replication of the PVX vector 10–14 days post bombardment. This showed that PVX can replicate in seed tissue and in as diverse plant species as *Glycine max* and *Nicotiana benthamiana*.

Introduction of Inverted Mutant Lox sites in PVX Amplicons

A mutant lox site (lox 43) was introduced by PCR into PVX-GFP amplicon. For this, PCR products I and II were made using pGV681 as the template and PCR primer pairs I [SEQ ID No:5 (GV70, upper primer) and SEQ ID No:6

(GV71, lower primer)] and II [SEQ ID No:7 (GV73, upper primer) and SEQ ID No:8 (GV72, lower primer)], respectively.

[SEQ ID No.5]5'-GCG GCA TGC GTC GAC ACA TGG TGG AGC ACG ACA-3' (GV70)

[SEQ ID No. 6]5'-GCC GGG TAC CGA GAC GCG TCA TCC CTT ACG-3' (GV71)

[SEQ ID No. 7]5'-GTC TCG GTA CCT ATA ATG TAT GCT ATA CGA AGT TAT ATA AGG AAG TTC ATT TCA-3' (GV73),

[SEQ ID No. 8]5'-TGA TCC GCG GGT TTC TTC TCA TGT-3' (GV72).

PCR product I was digested with SphI and Asp718 and PCR product II with Asp718 and Sac II to result in 369 bp and 464 bp fragments, respectively. pGV680 plasmid was digested with Sph I and Sac II and the 9792 bp vector fragment was ligated in a 3-way ligation with the two PCR fragments to yield plasmid pGV701 containing mutant lox 43 site between the As-1 element and the TATA box in 35S promoter of the amplicon.

A mutant lox site (lox 44) was inserted by adaptor ligation in the untranslated region 5' to the GUS ORF in pGV681. For this, pGV681 was digested with Xma I and ligated to an adaptor made by annealing the following two 51-mer primers:

[SEQ ID No. 9]5'-CCG GGA ATG CAT GCT ATA GCA TAC ATT ATA CGA AGT TAT TCG AAT TTA AAT-3'

[SEQ ID No. 10]5'-CCG GAT TTA AAT TCG AAT AAC TTC GTA TAA TGT ATG CTA TAG CAT GCA TTC-3'

Following Swa I digestion of the ligated DNA, the linear DNA was isolated, religated, and tranformed into *E. coli* to yield plasmid pGV700. Inserting lox 44 in PVX-GUS amplicon yielded a 31 amino acid-N-terminal extension of the GUS ORF. Mutant lox 43 and lox 44 sites in pGV700 and pGV701 were confirmed by DNA sequence analysis.

PVX-GFP and PVX-GUS amplicons with two inverted lox sites were made by combining the above mutant fox sites. Thus, for PVX-GUS, the Avr II-Sac I fragment, containing the GFP ORF, of pGV701was replaced with that of pGV700, carrying lox 44 and GUS ORF, yielding pGV702. For PVX-GFP, the 4432 bp Age I-Cla I fragment in pGV701 was replaced with the 4476 bp Age I-BstB 1 fragment, carrying lox 44, of pGV700, yielding pGV708 with a 23 amino acid-N-terminal extension of the GFP.

Detached leaves of *Nicotiana benthamiana* were bombarded with plasmids pGV700, pGV701, pGV702, and pGV708 using the biolistic gun. Based on expression of the reporter genes in the leaves 10–14 days after bombardment, replication was observed in all four cases, although the level of replication was lower in pGV708. These results show that insertion of lox sites in the plant promoter and/or in the intergenic sequence 5' to the reporter genes does not affect replication. The poorer GFP fluorescence in pGV708 may be due to the N-terminal extension on GFP protein.

To obtain a non-functional amplicon, pGV702 and pGV708 were passaged through Cre-expressing bacteria or incubated with purified Cre enzyme (Novagen, Madison Wis.) to invert the sequence between the inverted lox sites. However, no inversion was detected in either plasmid. This may be due to poor efficiency of inversion with these mutant lox sites that were the most inefficient in Cre-lox recombination.

Introduction of Inverted Wild Type Lox P sites in PVX Amplicons

A wild-type lox P site was cloned as an adaptor into the Cla I site in the intergenic region 5' to GFP ORF in plasmid pGV701 followed by Xma I digestion, isolation of the linear vector and its self ligation to yield plasmid pGV712. The adaptor was made by annealing primers GV78 (SEQ ID No.11) and GV77 (SEQ ID No.12)

[SEQ ID No. 11]5'-CGA TAA CTT CGT ATA ATG TAT GCT ATA CGA AGT TAT CCC GGG-3' (GV78)

[SEQ ID No. 12]5'-CGC CCG GGA TAA CTT CGT ATA GCA TAC ATT ATA CGA AGT TAT-3' (GV77)

The mutant lox 43 site in 35S promoter in pGV712 was replaced by a wild-type lox P site as follows. A PCR product was made on pGV712 DNA template using an upper primer GV74 (SEQ ID No. 13) and a lower primer GV72, (SEQ ID No.8).

[SEQ ID No. 13]5'-GAT GAC GCG TAT AAC TTC GTA TAA TGT-3' (GV74)

The PCR product was digested with Mlu I and Sac II, and the resulting product was used to replace the Mlu I-Sac II fragment containing lox 44 in pGV712 to yield plasmid pGV713. pGV713 contains two inverted wild-type lox P sites. Incubation of pGV713 with Cre recombinase as suggested by the manufacturer (Novagen, Madison, Wis.) inverted of the DNA sequence between the lox P sites containing the RNA dependent RNA polymerase to yield a non-functional amplicon in plasmid pGV714; Plasmid pGV714 was purified following transformation of *E. coli* XL 1 cells.

A wild-type lox P site was cloned as an adaptor into the Cla I site in the intergenic region 5' to GUS ORF in plasmid pGV702. For this plasmid pGV702 was linearized with Xma I, ligated to adaptor annealed from primers GV80 [SEQ ID NO: 14] and GV81 [SEQ ID NO: 15].

[SEQ ID No. 14]5'-CCG GGG ATA ACT TCG TAT AGC ATA CAT TAT ACG AAG TTA TTC GAA CAT TTA AAT-3' GV80

[SEQ ID No. 15]5'-CCG GAT TTA AAT GTT CGA ATA ACT TCG TAT AAT GTA TGC TAT ACG AAG TTA TCC-3' GV81

The resulting plasmid, designated pGV702W, was used to construct PVX-GUS with inverted wild-type lox P sites. For this, the Avr II-Sac I fragment, containing the GFP ORF, of pGV713 was replaced with that of pGV702W, carrying lox P and GUS ORF yielding pGV708W.

The inability of the inverted non-functional amplicons to replicate without undergoing Cre-mediated inversion to a functional amplicon was confirmed by bombardment of *Nicotiana benthamiana* leaves. Plasmids pGV712 and pGV713 replicated and spread in the bombarded leaves. This was clear from the showing that GFP fluoresence was detected 10–14 days after bombardment. However, plasmid pGV714 did not replicate unless co-bombarded with plasmid pNY102 that expresses Cre under the control of a 35S promoter. The 3.01 kB BspE1-Sac I fragment containing the inverted, non-functional amplicon from plasmid pGV714 was cloned into Xma I (BspE1 compatible)-Sac I cut pBE674, a binary vector with bar selection in plants, as described above, to result in pBE714. Plasmid pBE714 was introduced via agrobacterium LBA4404 in wild type *Nicotiana benthamiana* plants, as described above. The plants were selected on PPT 30 ug/ml phosphonithricin shooting and then 10 ug/ml rooting media. 10 transformants (714B #s E-5, E-6, G-1, M-4, M-6, M-7, Q-1, S-4, LL-1, UU-1were obtained. Southern analyses showed that all were positive for the transgene except for M-7 and Q-1. All appeared phenotypically normal and without any viral symptoms.

The ability of the transformants to be transactivated by Cre expression was tested using infection with PVX expressing Cre. Leaves from five positive 714 B transgenic plants (LL-1, UU-1, E-5, M-4, and S4) were bombarded with the particle gun using lug of a plasmid DNA carrying chimeric 35S:Cre gene to test for amplicon activation or with gold alone as a control. After ca. 5 days, GFP expression was noted in leaves of three (LL-1, M-4, and S4) of the five transgenic plants bombarded with 35S:Cre but not with gold alone control. After ca 12 days, the GFP expression in the transgenic leaves bombarded with 35S:Cre diminished, suggesting that silencing might was occuring, as is often seen upon infection of wild type leaves with PVX-GFP. The expression levels, spread, and duration of GFP in Cre-activated leaves were comparable to that of PVX:GFP bombarded directly into wild type *N. benthamiana* leaves.

Five out of eight T1 progeny seedlings of 714B transgenic LL-1 showed GFP expression upon bombardment with 35S:Cre. Similar bombardment of detached leaves from 12 other progeny seedlings showed that 11 were positive for activation. Thus, the inactive virus is heritable and the progeny capable of being Cre-activated. The expression levels, spread, and duration of GFP in Cre-activated seedlings was slightly variable between the T1 progeny individuals but were generally comparable to that of PVX:GFP bombarded directly into wild type *N. benthamiana* seedlings.

714B transgenic lines will be genetically combined with correctly regulated Cre chimeric genes, for example by crossing with transgenic lines carrying such Cre genes.

Example 3

Excisional Inactive Pvx Amplicons

To make a PVX RNA virus replicon flanked by tandem lox sites, two PCR products were made on pGV680: a 438 bp PCR product containing the TATA box ('minimal promoter') and lox P site using primer pairs GV85 [SEQ ID NO:16] (with Sph I site)-GV86 [SEQ ID NO: 17] (with Not I sites) and a 441 bp PCR product containing mutant lox site (loxD117) [Abrenski, K. and Hoess R. (1985) *J. Mol. Biol.* 184:211–220] and 5' end of the PVX cDNA using primer pairs GV87 [SEQ ID NO:18] (with Not I site)-GV88 [SEQ ID NO:19] (with Sac II site). Then, the two PCR products were digested with Not I, ligated, and used as template for PCR using primer pairs: GV105 [SEQ ID NO:20] and GV88 [SEQ ID NO:19] primers to give the 509 bp PCR product. The resultant PCR product was digested with Sph I and Sac II and the 509 bp fragment containing the TATA box ('minimal promoter') followed by tandem wild type and mutant (D117) lox P sites in front of the amplicon cDNA was isolated and cloned into Sph I-Sac II digested pGV680 to give pGV720. Thus, pGV720 is a PVX-GFP amplicon with minimal 35S promoter and tandem loxP and loxD117 sites between the TATA box and the transcription start site. pGV720 did not replicate efficiently when bombarded into *N. benthamiana*. Therefore, is was replaced with the full length promoter, which was isolated as a 438 bp PCR product using PCR primers GV85 [SEQ ID NO: 16] (with Sph I site) and GV86 [SE ID NO: 17] (with Not I site) on pGV680 and cloned into Sph I-Not I digested pGV720 to result in pGV740. Thus, pGV740 is a PVX-GFP amplicon with 35S promoter and tandem loxP and loxD117 sites between the TATA box and the transcription start site. pGV740 could replicate when bombarded into *N. benthamiana* even without a Cre expressing gene, suggesting that the amplicon can have at least 66 bp between the TATA box and the 5' end of PVX cDNA.

Although pGV740 may be readily inactivated by the insertion of a Transcriptional STOP fragment in the Not I site as represented in FIG. 3 it was decided to make an excisional replicon that physically excises the RNA virus amplicon from the chromosome upon site-specific recombination. For this, the promoter at the end of PVX cDNA was moved by first deleting the promoter by ligating a XmaI/NotI/XmaI adapter (primers GV157 [SEQ ID NO:21] & GVV158 [SEQ ID NO:22]) to the XmaI site of pGV740, followed by Not I digestion and religation. This resulted in pGV760, which is a promoter-less PVX-GFP amplicon with a mutant lox D117 site upstream of the transcription start site. Next a yeast 2u-trp fragment was isolated by PCR using primers GV 165 [SEQ ID NO:23] and GV166 [SEQ ID NO:24] and cloned by recombination around the Sph I site in Sph I- cut pGV760 by transforming the vector and target into yeast. DNA from yeast colonies prototrophic for trp was isolated and transformed into *E. coli*. Ampicillin-resistant *E. coli* were confirmed to be the desired yeast-*E. coli* shuttle plasmid, pGV774. A 391 bp of 35S promoter+lox P site was isolated by PCR using primers GV170 [SEQ ID NO:25] and GV171 [SEQ ID NO:26] on pGV740 with an Xma I site at 3' end of the lox P site and cloned by yeast recombination using 20 bp overlaps to regions flanking the Nar I site in pGV774. The resultant plasmid, pGV783, is a yeast-*E. coli* shuttle vector containing a floxed, excisional PVX-GFP amplicon flanked by tandem WT and lox D117 sites. As an excisonal amplicon is represented by element B with or without elements A and/or C in FIG. 1.

Inactive Movement-defective Excsional PVX Amplicon

The coat protein gene in excisional PVX-GFP amplicon in pGV783 was deleted by Xho I and Sal I digestion of pGV783 followed by religation to result in a movement-defective amplicon, pGV819. This mutant amplicon was isolated as a Xma I fragment and cloned into the Xma I site of pBIN19 binary vector to result in pBE819. This was introduced into tobacco plants via agrobacterium-mediated transformation.

Inactive Excsional PVX Amplicon with Dual Reporters for Foreign Protein Expression To demonstrate that the amplicons can be used to both express a foreign protein as well as silence an endogenous gene, pGV784 was made. This construct is a yeast-*E. coli* shuttle vector containing a floxed excisional PVX- CP-GFP-PDS amplicon with WT and lox D117 sites. The Avr II/SacI 3.6 kb band from pGV770 was cloned into the Avr II/Sac I cut pGV783. pGV770 is PVX-GFP-PDS-CP amplicon. It contains a chimera of the GFP ORF (740 bp) followed by a ca. 200 bp fragment of partial *N. benthamiana* phytoene desaturase cDNA. It was constructed by two-step PCR. First, the entire GFP ORF was isolated by PCR on plasmid pGV680 using primer pairs GV162 [SEQ ID NO:27]/ GV163 [SEQ ID NO:28] and a 200 bp *N. benthamiana* phytoene desaturase sequenced was isolated by PCR using primer pairs GV133 [SEQ ID NO:29]/GV109 [SEQ ID NO:30] on plasmid pGV723 that carries a partial *N. benthamiana* phytoene desaturase cDNA clone [Ruiz et. al. (1998) *Plant Cell* 10:937–946], since the 3' 18 bp sequence of these primers is specific for the phytoene desaturase sequence, these 18 bp sequences can also be used isolating the sequence directly by RT-PCR from mRNA isolatedfiom *N. benthamiana* leaf, by techniques well known by one skilled in the art. Next, these 2 fragments were ligated by Age I/Xma I sites introduced by the primers and re-amplified by PCR using GV162 [SEQ ID NO:27] and GV109 [SEQ ID NO:30]. The entire chimeric GFP-PDS fragment was digested with Cla I and Xho I and cloned into the Cla I-Sal I sites of pVX201 to result in pGV770. The Avr II/Sac I 3.6 kb band from pGV770 was cloned into the Avr II/Sac I cut pGV783 (see below) to result in plasmid pGV784. In this case, the excsional amplicon in pGV784 represents element B without elements A and C in FIG. 1. It was isolated as a 8.387 kB Xma I fragment and cloned into Xma I site of pBin19 binary vector to result in pBE784, which was introduced into tobacco via agrobacterium-mediated transformation.

Primers referred to in the above discussion are given below:

GV85

5'-GAG GCA TGC CCG GGC AAC ATG GTG GAG CAC GAC A-3'     [SEQ ID NO: 16]

GV86

5'-TAT GCG GCC GCA TAA CTT CGT ATA GCA TAC ATT ATA CGA AGT TAT ATA GAG GAA GGG T-3'     [SEQ ID NO: 17]

GV87

TCC TTG ATC CGC GGG TTT CTT CTC ATG T     [SEQ ID NO: 18]

GV88

5'-TCC TTG ATC CGC GGG TTT CTT CTC ATG T-3'     [SEQ ID NO:19]

GV105

5'-CAC GCA TGC ACT ATC CTT CGC AAG ACC C-3'     [SEQ ID NO:20]

GV157

5'-CCG GGG CGG CCG CAT AC-3'     [SEQ ID NO:21]

GV158

5'-CCG GGT ATG CGG CCG CC-3'     [SEQ ID NO:22]

GV165

5'-ACC ATG ATT ACG CCA AGC TTA AGA AAA GGA GAG GGC CAA GA-3'     [SEQ ID NO:23]

GV166

5'-AGT TAT GCG GCC GCC CCG GGC ATA TGA TCC AAT ATC AAA GGA-3'     [SEQ ID NO:24]

GV170

5'-GCG CAG CCT GAA TGG CGA ATG GCG CCC AAA AAA TAT CAA AGA TAC A-3'     [SEQ ID NO:25]

GV171

5'-AAG GAG AAA ATA CCG CAT CAC CCG GGA TAA CTT CGT ATA GCA TAC A-3'     [SEQ ID NO:26]

GV162 (25-mer)

5'-GCC AAT CGA TCA TGA GTA AAG GAG A-3'     [SEQ ID NO:27]

GV163 (35-mer)

5'-GCT AAC CGG TAG ACA TTT ATT TGT ATA GTT CAT CC-3'     [SEQ ID NO:28]

GV133 (34-mer)

5'-GAA GTC GAC CGC GGG CAG ACT AAA CTC ACG AAT A-3'

GV109 (30-mer)

5'-GAA TTC TCG AGC CAT ATA TGG ACA TTT ATC-3'     [SEQ ID NO:30]

Example 4

Co-Activation of an Inactive PVX Replicon and Silenciny Suppresser Gene by Site-Specific Recombination A silencing suppresser gene will be incorporated into the lox-containing PVX amplicons by two methods. In one method, the ORF of a silencing suppressor will replace the target gene or coat protein ORF in amplicons depicted in FIGS. 1–3 such that the silencing suppresser is on the replicon. In the second method, the ORF of a silencing suppressor will replace the excsional reporter, such that it is represented by element C and the floxed amplicon acting as a transcriptional/translational Stop fragment, is represented by element B in FIG. 1. In either case, activation of the amplicon will also activate expression of the silencing suppressor gene for overcoming host's antiviral defense system involving homology dependent silencing and result in higher replication and higher foreign protein production.

Co-Activation of an Inactive (Inverted) PVX Replicon and Silencing Suppresser Gene by Site-Specific Recombination pGV714 is a non-functional PVX-GFP amplicon with inverted lox P sites, whose construction is described above. It was used to make coat protein replacement vectors, pGV806 and pGV808. For pGV806, the ORF of the coat protein in pGV714 was replaced with that of silencing suppressor HC-Pro (bases 1057–2433 of tobacco etch virus genome, Gen Bank accession number M15239) or P1-HC-Pro (bases 145–2433 of tobacco etch virus genome, Gen Bank accession number M15239) isolated from plasmid Ptl-0059 (American Type Culture Collection, ATCC 45035). This cloning was done by homologous recombination in yeast [Hua, S. B., et al., (1997) Plasmid 38(2):91–6; Oldenburg, K. R., et al., (1997) *Nucleic Acids Res* 25(2) :451–2, and Prado, F., et al., (1 994) *Curr Genet* 1994 February;25(2):180–3]. For this, first a PCR fragment containing the yeast selection marker (trp) and 2 micron yeast origin of replication was made by using PCR primers P216 and P217 [SEQ ID Nos 31 and 32]. The 5' 25 bases of these primers have homology to either side of the Kas I in the *E. coli* vector of pGV714, such that co-transformation of the PCR product into yeast cells alongwith Kas I-linearized pGV714 resulted in the cloning of the yeast fragment by gap reapir (homologous recombination across the Kas I site in the vector) resulting in an *E. coli*-yeast shuttle vector, pGV800. Next, PCR products containing HC-Pro or P1-HC-Pro were made by using PCR primer pairs P233-P235 [SEQ ID NO:33 and 35 respectively] and P234-P235 [SEQ ID NO:34 and 35 respectively], respectively, on pTL-0059. The 33 5' -terminal bases in P233 and 30 5'-terminal bases in P234 are homologous to the coat protein promoter, while 31 5'-terminal bases in 235 are homologous to the 3' UTR of the coat protein ORF. Co-transformation of HC-Pro or P1-HC-Pro PCR products alongwith Stu I linearized pGV800 resulted in gap repair (homologous recombination across the Stu I site in the coat protein ORF) and replacement of the coat protein coding sequence with that of HC-Pro or P1-HC-Pro to result in pGV806 and pGV808, respectively. These silencing suppressors replace the coat protein ORF in amplicons represented by FIG. 2.

Primers referred to in the preceding discussion are given below:
P216(46-mer)

5-<u>TGC GTA AGG AGA AAA TAC CGC ATC AAA GAA AAG GAG AGG GCC AAG A</u>-3'  [SEQ ID NO:31]

The 25 5'-terminal bases (underlined) are homologous to pGV714 vector, and 21 3'-bases are homologous to the yeast fragment.

P217(47-mer)

5'-<u>GCG CAG CCT GAA TGG CGA ATG GCG CCA TAT GAT</u> CCA ATA TCA AAG GA-3'  [SEQ ID NO:32]

The 25 5'-terminal bases (underlined) are homologous to pGV714 vector, and 22 3'-bases are homologous to the yeast fragment.
P233 (52 bp UP for HCP)

5'-<u>AAC GGT TAA GTT TCC ATT GAT ACT CGA AAG ATG</u> AGC GAC AAA TCA ATC TCT GA-3"  [SEQ ID NO:33]

The 33 5'-terminal bases (underlined) are PVX coat protein promoter in pGV800 and 20 3'-bases are homologous to 5' terminus of HC-Pro coding sequence.
P234 (50 bp UP for P1-HC-Pro)

5'-<u>AAC GGT TAA GTT TCC ATT GAT ACT CGA AAG</u> ATG GCA CTG ATC TTT GGC AC-3"  [SEQ ID NO:34]

The 30 5'-terminal bases (underlined) are homologous to PVX coat protein promoter in pGV800 and 20 3'-bases are homologous to 5' terminus of P1-HC-Pro coding sequence.
P235 (53 bp LP for HCP)

5'-<u>GGG GTA GGC GTC GGT TAT GTA GAC GTA GTT</u> ATC CAA CAT TGT AAG TTT TCA TT-3"  [SEQ ID NO:35]

The 31 5'-terminal bases (underlined) are homologous to 3'-UTR of PVX coat protein sequence in pGV800 and 22 3'-bases are homologous to 3' terminus of HC-Pro coding sequence.

These modified PVX cDNAs carrying GFP and silencing suppressors without coat protein will be used to transform tobacco plants via agrobacterium-mediated transformation known to one skilled in the art. For example, the amplicon in pGV806 was isolated as a 8.3 kB BspeI and Xma I fragment and cloned into Xma I linearized pBIO1. Upon controlled Cre-mediated recombination, co-activation of viral replication without systemic spread and of silencing suppressor will enhance foreign protein, in this case GFP production.

Co-Activation of an Inactive, Excisional PVX Replicon and Silencing Suppresser Gene by Site-Specific Recombination The entire region between the lox sites containing the PVX cDNA and the 35S promoter from plasmid pGV783 can be isolated and cloned between lox sites, as element B, with elements A and/or C in FIG. 1. For this, the sequence of and around the lox sites before excision will be:

atg<u>ATAACTTCGTATAGCATACATTATACGAAGT TAT</u> [SEQ ID NO:36]-inactive PVX amplicon -TAANTAA<u>ATAACTTCGTATAGCATACATTATACGA AGTTAT</u> [SEQ IDNO:37] Q; and after excision it is:

atg<u>ATAACTTCGTATAGCATACATTATACGAAGTTAT</u> [SEQ ID NO:38] Q;

where the lowercase codon is the initiation codon, the underlined sequences are the wild type lox P site flanking the inactive replicon, N is any base, and Q is the coding sequence of the silencing suppressor, such that it is in-frame to the initiation codon after excision. Thus, the silencing suppresser is not translated unless the blocking fragment is excised to restore its proper reading frame. The wild type lox sequence will also be replaced by mutant ones for enhanced conditional specificity while preserving this translational activation by methods known to one skilled in the art.

Example 5

Co-Activation of an Inactive (Floxed) Geminivirus

Replicon And Silencing Sunpresser Gene by Site-Specific Recombination: Suppresser Gene Is on the Replicon A silencing suppresser gene will be incorporated into the floxed geminivirus vector by two methods. The ORF of a silencing suppressor will replace either the GUS ORF or the luciferase ORF in pGV733. In the former case, the silencing suppresser is on the replicon (as an element B with or without elements A and/or C in FIG. 1. While in the latter case, it is outside the replicon, as element C alongwith elements A and B in FIG. 1, such that element B acts as a transcriptional/translational Stop fragment. An example of translational stop fragment is as described above for PVX. In either case, activation of the replicon will also activate expression of the silencing suppressor gene for overcoming host's antiviral defense system involving homology dependent silencing and result in higher replication and higher foreign protein production.

Example 6

Floxed Binary TGMV with GFP Replacing the Coat Protein

A coat replacement vector of TGMV was made with GFP. For this a PCR fragment containing the yeast selection marker (trp) and 2 micron yeast origin of replication was made by using PCR primers P216 and P217 [SEQ ID NO:31 and 32] and cloned into the Kas I in the *E. coli* vector in pCSTA [Von Arnim, Albrechit; Stanley, John. *Virology* (1992), 186(1), 286–93], obtained from Dr. John Stanley (John Innes Center, Norwich, United Kingdom) by gap reapir (homologous recombination across the Kas I site in the vector, as described previously) resulting in an *E. coli*-yeast shuttle vector, pGV793. Next, a PCR product containing 796 bp GFP ORF was made from plasmid psmGFP [Davis, S. J. and Vierstra, R. D. (1998) *Plant Molecular Biology* 36:521–528] with primers P218 [SEQ ID NO:39] and P219 [SEQ ID NO:40] and cloned into Hpa I+BstB1 cut pGV793 by yeast cloning to result in pGV798. P218 is a 49 bp primer whose 5' 29 bases is homologous to the coat protein promoter and 3' 18 bp has homology to 5' end of GFP ORF (except for 2 bp mismatch), while P219 is a 48-mer, whose 5' 31 bases is homologous to coat protein 3' untranslated region and 3' 18 bases are homologous to the 3' end of GFP ORF. Finally, the Sac I-Nhe I fragment coat protein in pGV651, a TGMV-A dimer (PCT Int. Appl. WO 99/22003) was replaced with that from pGV798 to make pGV802, a TGMV-A dimer with GFP replacing the coat protein.

When *N. benthamiana* was co-bombarded with pGV802 and TGMV-B dimer (obtained from Dr. D. Robertson, North Carolina State University), infected tissue expressed GFP that was persistent and did not silence for at least 2 months. To make a floxed TGMV-GFP replicon, a single copy of the replicon will be isolated as a Mfe I partial and cloned into the Eco RI site of pGV690, as described above. The Bam HI-Xho I fragment containing GFP ORF of the resulting plasmid will be used to replace the GUS ORF in pBE733, cut with Bam HI and Xho I. This binary vector will be transformed into plants via agrobacterium-mediated transformation alone or co-transformed with plasmid pBE795. pBE795 is a binary vector containing TGMV-B dimer. It was made by the replacing the Sma I to Sal I sequence of pBIB, [Becker, D. (1990) Nucleic Acids Research 18:203] with that of BsrB I to Sal I fragment of TGMV B dimer.

P218 (UP primer for GFP ORF)(49-mer)

5'-AAA GTT ATA TAA AAC GAC ATG CGT TTC GTA GAT CTA AGG AGA TAT AAC A-3' [SEQ ID NO:39]

P219 (LP for GFP ORF) (48-mer)

5'-AAT TTT ATT AAT TTG TTA TCG AAT CAT AAA TTA TTT GTA TAG TTC ATC-3' [SEQ ID NO:40]

Example 7

Transpenic Lines Expressing Regulated Chimeric Cre Genes

For chimeric replicase genes the Cre ORF was isolated as a 1.3 kB Nco I-Xba I fragment from a 35S:Cre plasmid and used to replace the Nco I-Xba I fragment containing the 10 kD ORF in pGV656 and the Nco I-Xba I fragment containing the ACMV replication protein in pGV659 to result in plasmids pGV692 and pGV693, respectively. The Hind III fragment from pGV692 containing the Vc:Cre gene was cloned into the Hind III site of pBin19 (GEN BANK ACCESSION U09365) and pBE673 (described in PCT Int. Appl. WO 99/22003) to yield binary plasmids pBE692 (with plant kanamycin resistance gene) and pBE692b (with plant phosphothricon resistance gene), respectively. The Bam HI-Bam HI-Asp718 I partial fragment from pGV693 containing the IN:Cre gene cloned into Bam HI-Asp718 I cut pBin19 and pBE673 to yield binary plasmids pBE693 and pBE693b, respectively. *Nicotiana benthamiana* and *N. tabacum* var *Xanthi* were transformed with agrobacterium BA692 and BA693 containing binary plasmids pBE692 and pBE693, respectively. These transgenic plants will be crossed with those carrying the floxed viruses.

A chimeric IN:Cre gene was modified to reduce its translationability in order to tolerate leaky Cre transcription. Since, it has been reported that small upstream ORFs usually reduce, or in extreme cases preclude, downstream translation [Kozak, M. (1996) *Mammalian Genome*, 7, 563–74], pGV693 was linearized with the unique Nco I site at the initiation codon of the Cre ORF and ligated an adapter made up of primers P224 [SEQ ID NO:41] and P225 [SEQ ID NO:42]. This resulted in the addition of 39 bp sequence upstream of the translation initiation codon including 21 bp ORF 18 bp upstream of the translation initiation codon. The modification in the resultant plasmid, pGV787, was confirmed by DNA sequencing. Bam HI fragment from pGV787 was used to replace the corresponding region in pBE673 to yield pBE787 binary vector. This vector was tested in transgenic plants.

Primers used in the preceeding discussion are given below:

P224

5'-CAT GCG TGT CGC ATA CTA TTA CTA ATA GGC AGC GAG GAT-3' [SEQ ID NO:41]

P225

5'-CAT GAT CCT CGC TGC CTA TTA GTA ATA GTA TGC GAC ACG-3' [SEQ ID NO42]

Screening for Correctly Regulated Cre Expression and Use of Mutant Lox Sites

A system was developed to enable the selection of transgenic lines that have correctly regulated Cre expression. The luciferase gene was chosen as a sensitive, non-destructive reporter for Cre-mediated excision. A set of floxed vectors, pGV751–754, that contain the basic cassette "35S promoter-lox-NPT II gene-rbcS 3' terminator-Nos 3' terminator-lox-Luc" were chosen. Cre expression would excise the 'STOP' fragment containing NPT II gene and the transcriptional terminator sequences between the lox sites, thus, switching on luciferase expression. Thus, the excision of NPT II gene during selection will render the plants sensitive to kanamycin selection. Co-transformation of these bar-resistant binary vectors carrying IN2:Cre (pBE692) or Vc:Cre (pBE693), as described previously, on kanamycin+bar selection plates allowed for the selection of transgenic lines where Cre expression is low enough not to mediate recombination.

Using the above selection method the efficacy of mutant lox sites to improve the 'specificity' of the regulated promoters expressing Cre was tested. Several mutant lox sites have been published that have been reported to require more Cre protein to activate the site-specific recombination [Albert et al., *Plant. J.* 7:649–59 (1995)]. For example, the in vitro efficiency of mutant sites, lox 72, lox 78, and lox 65 sites were reported to be 12.5%, 5%, and 2.5%, respectively, relative to wild type lox P. Plasmids pGV751, pGV752, pGV753, and pGV754 contain one wild type lox site and a second lox site that is wild type lox P, lox 65, lox 72, and lox 78, respectively, in the above cassette. pGV751 and pGV752 were selected for initial testing in transgenic plants. The floxed constructs were introduced in binary vectors (referred below with pBE prefix) and transformed into tobacco (*N. tabacum*, cv. *Xanthi*) plants via agrobacterium-mediated leaf disc transformation with pBE751 (kan)+pBE693b (bar), pBE751 (kan)+pBE692b (bar), pBE753 (kan)+pBE693b (bar), and pBE753 (kan)+pBE692b (bar).

For safener induction leaf discs of primary transformants were flooded for 30 min in 30 ppm of freshly made 2-CBSU [Hershey, H. P. and Stoner, T. D. (1991) *Plant Molecular Biology* 17:679–690] and then placed on solid plain MS medium for 1–2 days before assay. Whole seedling or leaf discs to be tested were sprayed with 5 mM beetle luciferin and then kept in dark for 5 min before imaging for luciferase expression under a cool CCD camera.

Results of 751/693Bar and 753/693Bar Cotransformation

Expression of luciferase was detected by a cool CCD camera from untreated and safener-treated independent transgenic lines transformed with IN:Cre in the presence of floxed construct pBE751 (with wild type lox P site) or pBE753 (with mutant lox 72). Table 1 shows that relative to wild type lox P mutant lox 72 reduces the number of lines that show luciferase in leaf discs at zero time point. Lines that showed safener inducibility with no background were selected for further analysis. Leaf discs from these plants were incubated for 2 days with or without safener treatment. Table 2 shows that luciferase expression, a reporter of excision, is higher in lines co-transformed with pBE751 than with pBE753.

TABLE 1

Luciferase expression in leaf discs with or without treatment with safener

| independent transgenic plants | | no treatment | 2-CBSU and wounding treatment |
|---|---|---|---|
| 751 and 693 bar | 1d | − | + |
| | 8b | + | + loxed? |
| | 10a | − | + |
| | 11a | − | − |
| | 16a | + | + loxed? |
| | 20 | − | − |
| | 21 | − | + |
| | 26c | − | + |
| | 29a | + | + loxed? |
| | 30 | − | + |
| | 31 | + | + loxed? |
| | 32 | + | + loxed? |
| | 33 | + | + loxed? |
| | 34 | + | + loxed? |
| | 35 | + | + loxed? |
| | 36 | − | − |
| | 37 | − | + |
| 753 and 693 bar | 1b | − | − |
| | 4b | − | +/− |
| | 6a | − | +/− |
| | 12a | − | − |
| | 14d | − | + |
| | 17a | − | − |
| | 18c | − | + |
| | 21a | − | − |
| | 22 | − | + |
| | 23a | − | + |
| | 24b | − | − |
| | 26a | − | − |
| | 29b | − | − |
| | 30 | − | +/− |
| | 31 | − | − |
| | 32 | − | +/− |

TABLE 2

Relative luciferase expression in leaf discs with or without treatment with safener after 2 days

| | wounding | 2-CBSU and wounding |
|---|---|---|
| control 1 (wt) | 187 | 218 |
| * control 2 | 126 | 283 |
| 751 1 | 5,663 | 4,895 |
| 751 10 | 1,156 | 5,522 |
| 751 21 | 1,286 | 16,500 |
| 751 26 | 1,898 | 6,990 |
| 751 30 | 2,595 | 58,015 |
| 751 37 | 8,450 | 72,091 |
| 753 4 | 829 | 921 |
| 753 6 | 247 | 671 |
| 753 14 | 495 | 4,408 |
| 753 18 | 905 | 8,598 |
| 753 22 | 241 | 1,274 |
| 753 23 | 405 | 3,843 |
| 753 30 | 542 | 1,117 |
| 753 32 | 129 | 645 |

* Control 2 is a transgenic plant with 751/693 bar. However, luciferase in this transgenic plant is not induced either by wounding or safener-treatment.

What is claimed is:

1. A binary viral expression system comprising:
   (i) a chromosomally-integrated inactive replicon, derived from viruses selected from the group consisting of geminiviruses and single-stranded RNA viruses, the inactive replicon comprising:
      a) cis-acting viral elements required for viral replication;
      b) a target gene comprising at least one regulatory sequence; and
      c) site-specific sequences responsive to a site-specific recombinase; and
   (ii) a chromosomally-integrated chimeric transactivating gene comprising a regulated plant promoter operably-linked to a site-specific recombinase coding sequence;
   wherein expression of the chimeric transactivating gene in cells containing the inactive replicon results in site-specific recombination which releases the inactive replicon from the chromosome, activates replicon replication, and increases expression of the target gene.

2. The binary viral expression system of claim 1 wherein the site-specific sequences responsive to the recombinase are lox sequences and the site-specific recombinase coding sequence encodes for the Cre protein.

3. The binary viral expression system of claim 1 wherein the geminivirus is selected from the group consisting of TGMV and ACMV.

4. The binary viral expression system of claim 1 wherein the single-stranded RNA virus is potato virus X.

5. The viral expression system of claim 1 wherein the regulated plant promoter is selected from the group consisting of tissue-specific promoters, inducible promoters, and development stage-specific promoters.

6. The binary viral expression system of claim 5 wherein the regulated promoter is derived from genes selected from the group consisting of: genes derived from a safener-inducible system, genes derived from the tetracycline-inducible system, genes derived from salicylate-inducible systems, genes derived from alcohol-inducible systems, genes derived from glucocorticoid-inducible system, genes derived from pathogen-inducible systems, and genes derived from ecdysone-inducible systems.

7. The binary viral expression system of claim 1 wherein the target gene encodes a protein selected from the group consisting of an enzyme, a structural protein, a seed storage protein, a protein that conveys herbicide resistance, and a protein that conveys insect resistance.

8. The viral expression system of claim 1 wherein the at least one regulatory sequence linked to the target gene is selected from the group consisting of constitutive plant promoters, plant tissue-specific promoters, plant development-specific promoters, inducible plant promoters and viral promoters.

9. The binary viral expression system of claim 8 wherein the at least one regulatory sequence is selected from the group consisting of a viral coat protein promoter, the nopaline synthase promoter, the phaseolin promoter, and the cauliflower mosaic virus promoter.

10. The binary viral expression system of claim 1 wherein the target gene is operably linked to a DNA fragment encoding a transit peptide.

11. A method of altering the levels of a protein encoded by a target gene in a plant comprising:
    (i) transforming a plant with the viral expression system of claim 1 and
    (ii) growing the transformed plant seed under conditions wherein the protein is expressed.

12. The method of claim 11 wherein the site-specific sequences responsive to the recombinase are mutant lox sequences that are inefficient for Cre-lox recombination and the site-specific recombinase coding sequence encodes the Cre protein.

13. A method of altering the levels of a protein encoded by a target gene in a plant comprising:
    (i) transforming a first plant with a inactive replicon to form a first primary transformant, the inactive replicon derived from viruses selected from the group consisting of geminiviruses and single-stranded RNA viruses, comprising:
       a) cis-acting viral elements required for viral replication;
       b) a target gene comprising at least one regulatory sequence; and
       c) site-specific sequences responsive to a site-specific recombinase,
    (ii) transforming a second plant with a chimeric transactivating gene to form a second primary transformant comprising a regulated plant promoter operably-linked to a transactivating site-specific recombinase coding sequence;
    (iii) growing the first and second primary transformants wherein progeny from both seeds are obtained; and
    (iv) crossing the progeny of the first and second transformants wherein the target gene is expressed.

14. The binary transgenic expression system of claim 1 wherein the chromosomally-integrated inactive replicon is inserted into a reporter gene sequence such that when the replicon is excised the reporter gene is activated.

15. The binary transgenic expression system of claim 1 wherein a Transcription Stop Fragment is inserted in the inactive replicon.

16. A binary transgenic viral expression system comprising:
    (i) a chromosomally-integrated inactive replicon derived from viruses selected from the group consisting of geminiviruses and single-stranded RNA viruses, the inactive replicon comprising:
       a) cis-acting viral elements required for viral replication;
       b) a target gene comprising at least one regulatory sequence; and
       c) site-specific sequences responsive to a site-specific recombinase; and
    (ii) a transiently-expressed chimeric transactivating gene comprising a plant or viral promoter operably-linked to a site-specific recombinase coding sequence;
    wherein expression of the chimeric transactivating gene in cells containing the inactive replicon results in the site-specific recombination, activation of replicon replication, and increased expression of the target gene.

17. A method of altering the levels of a protein encoded by a target gene in a plant comprising:
    (i) transforming a plant with a inactive replicon derived from viruses selected from the group consisting of geminiviruses and single-stranded RNA viruses, the inactive replicon comprising:
       a) cis-acting viral elements required for viral replication;
       b) a target gene comprising at least one regulatory sequence; and
       c) site-specific sequences responsive to a site-specific recombinase;
    (ii) infecting the transformant with a virus containing a chimeric transactivating gene comprising a regulated plant promoter operably-linked to a transactivating site-specific recombinase coding sequence;

wherein expression of the chimeric transactivating gene in cells containing the inactive replicon results in the site-specific recombination, activation of replicon replication, and increased expression of the target gene.

18. A binary transgenic viral replication system comprising:
   (i) a chromosomally-integrated inactive replicon derived from viruses selected from the group consisting of geminiviruses and single-stranded RNA viruses, the inactive replicon comprising cis-acting viral elements required for viral replication and site-specific sequences responsive to a site-specific recombinase; and
   (ii) a chimeric transactivating gene, comprising a regulated plant promoter operably-linked to a site-specific recombinase coding sequence;
wherein expression of the chimeric transactivating gene in cells containing the inactive replicon results in the site-specific recombination and activation of replicon replication.

19. The method of claim 18 wherein the site-specific sequences responsive to the recombinase are lox sequences.

20. The transgenic viral replication system of claim 18 wherein the geminvirus is selected from the group consisting of TGMV and ACMV.

21. The transgenic viral replication system of claim 18 wherein the single-stranded RNA viruses is a potato virus X.

22. The viral replication system of claim 18 wherein the regulated plant promoter is selected from the group consisting of tissue-specific promoters, inducible promoters, and development stage-specific promoters.

23. The viral replication system of claim 22 wherein the regulated promoter is derived from genes selected from the group consisting of: genes derived from a safener-inducible system, genes derived from the tetracycline-inducible system, genes derived from salicylate-inducible systems, genes derived from alcohol-inducible systems, genes derived from glucocorticoid-inducible system, genes derived from pathogen-inducible systems, and genes derived from ecdysone-inducible systems.

24. A method of increasing viral resistance in a plant comprising:
   (i) transforming a first plant with an inactive replicon, the inactive replicon derived from viruses selected from the group consisting of geminivirus and single-stranded RNA viruses, to form a first primary transformant, the inactive replicon comprising:
      a) cis-acting viral elements required for viral replication;
      a viral nucleotide sequence encoding a product that confers increased viral resistance, operably linked to a regulatory sequence;
      c) site-specific sequences responsive to a site-specific recombinase;
   (ii) transforming a second plant with a chimeric transactivating gene to form a second primary transformant comprising a regulated plant promoter operably-linked to a transactivating site-specific recombinase coding sequence;
   (iii) growing the first and second primary transformants wherein progeny from both seeds are obtained; and
   (iv) crossing the progeny of the first and second transformants wherein the viral nucleotide sequence is expressed, conveying increased viral resistance to the plant.

25. A binary viral expression system comprising:
   (i) a chromosomally-integrated inactive replicon, derived from viruses selected from the group consisting of geminiviruses and single-stranded RNA viruses, the inactive replicon comprising:
      a) cis-acting viral elements required for viral replication;
      b) a target gene comprising:
         1) at least one regulatory sequence; and
         2) a coding sequence operably linked to said regulatory sequence; and
      c) site-specific sequences responsive to a site-specific recombinase; and
   (ii) a chromosomally-integrated chimeric transactivating gene comprising a regulated plant promoter operably-linked to a site-specific recombinase coding sequence;
wherein expression of the chimeric transactivating gene in cells containing the inactive replicon results in site-specific recombination which releases the inactive replicon from the chromosome, activation of replicon replication, and expression of the coding sequence, which causes post-transcriptional gene silencing of a transgene or endogenous gene.

* * * * *

SEQUENCE LISTING

<160> NUMBER OF SEQ ID NOS: 42

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 1
tcgagataac ttcgtataat gtatgctata cgaagttatg        40

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 2
aattcataac ttcgtatagc atacattata cgaagttatc        40

<210> SEQ ID NO 3
<211> LENGTH: 45
<212> TYPE: DNA
<213> ORGANISM: Artificial Sequence
<220> FEATURE:

-continued

<223> OTHER INFORMATION: Description of Artificial Sequence: Primer

<400> SEQUENCE: 3
aattctataa cttcgtataa tgtatgctat acgaagttat gagct          45

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 4
cataacttcg tatagcatac attatacgaa gttatag          37

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 5
gcggcatgcg tcgacacatg gtggagcacg aca          33

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 6
gccgggtacc gagacgcgtc atcccttacg          30

<210> SEQ ID NO 7
<211> LENGTH: 54
<212> TYPE: DNA
<213> ORGANISM: Artificial Sequence
<220> FEATURE:
<223> OTHER INFORMATION: Description of Artificial Sequence: Primer

<400> SEQUENCE: 7
gtctcggtac ctataatgta tgctatacga agttatataa ggaagttcat ttca          54

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 8
tgatccgcgg gtttcttctc atgt          24

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 9
ccgggaatgc atgctatagc atacattata cgaagttatt cgaatttaaa t          51

```
<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 10
ccggatttaa attcgaataa cttcgtataa tgtatgctat agcatgcatt c          51

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 11
cgataacttc gtataatgta tgctatacga agttatcccg gg                    42

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 12
cgcccgggat aacttcgtat agcatacatt atacgaagtt at                    42

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 13
gatgacgcgt ataacttcgt ataatgt                                     27

<210> SEQ ID NO 14
<211> LENGTH: 54
<212> TYPE: DNA
<213> ORGANISM: Artificial Sequence
<220> FEATURE:
<223> OTHER INFORMATION: Description of Artificial Sequence: Primer

<400> SEQUENCE: 14
ccggggataa cttcgtatag catacattat acgaagttat tcgaacattt aaat       54

<210> SEQ ID NO 15
<211> LENGTH: 54
<212> TYPE: DNA
<213> ORGANISM: Artificial Sequence
<220> FEATURE:
<223> OTHER INFORMATION: Description of Artificial Sequence: Primer

<400> SEQUENCE: 15
ccggatttaa atgttcgaat aacttcgtat aatgtatgct atacgaagtt atcc       54

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Primer
```

<400> SEQUENCE: 16
gaggcatgcc cgggcaacat ggtggagcac gaca                         34

<210> SEQ ID NO 17
<211> LENGTH: 58
<212> TYPE: DNA
<213> ORGANISM: Artificial Sequence
<220> FEATURE:
<223> OTHER INFORMATION: Description of Artificial Sequence: Primer

<400> SEQUENCE: 17
tatgcggccg cataacttcg tatagcatac attatacgaa gttatataga ggaagggt    58

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 18
tccttgatcc gcgggtttct tctcatgt                                28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 19
tccttgatcc gcgggtttct tctcatgt                                28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 20
cacgcatgca ctatccttcg caagaccc                                28

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 21
ccggggcggc cgcatac                                            17

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 22
ccgggtatgc ggccgcc                                            17

<210> SEQ ID NO 23
<211> LENGTH: 41

```
<212> TYPE: DNA
<213> ORGANISM: Artificial Sequence
<220> FEATURE:
<223> OTHER INFORMATION: Description of Artificial Sequence: Primer

<400> SEQUENCE: 23
accatgatta cgccaagctt aagaaaagga gagggccaag a                   41

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 24
agttatgcgg ccgccccggg catatgatcc aatatcaaag ga                  42

<210> SEQ ID NO 25
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 25
gcgcagcctg aatggcgaat ggcgccccaa aaatatcaaa gataca              46

<210> SEQ ID NO 26
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 26
aaggagaaaa taccgcatca cccgggataa cttcgtatag cataca              46

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 27
gccaatcgat catgagtaaa ggaga                                     25

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 28
gctaaccggt agacatttat ttgtatagtt catcc                          35

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 29
```
gaagtcgacc gcgggcagac taaactcacg aata                          34

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 30
gaattctcga gccatatatg gacatttatc                               30

<210> SEQ ID NO 31
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 31
tgcgtaagga gaaataccg catcaaagaa aaggagaggg ccaaga              46

<210> SEQ ID NO 32
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 32
gcgcagcctg aatggcgaat ggcgccatat gatccaatat caaagga            47

<210> SEQ ID NO 33
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 33
aacggttaag tttccattga tactcgaaag atgagcgaca aatcaatctc tga      53

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 34
aacggttaag tttccattga tactcgaaag atggcactga tctttggcac          50

<210> SEQ ID NO 35
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 35
ggggtaggcg tcggttatgt agacgtagtt atccaacatt gtaagttttc att      53

<210> SEQ ID NO 36
<211> LENGTH: 37
<212> TYPE: DNA
<213> ORGANISM: Artificial Sequence

```
<220> FEATURE:
<223> OTHER INFORMATION: Description of Artificial Sequence: Primer

<400> SEQUENCE: 36
atgataactt cgtatagcat acattatacg aagttat                    37

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 37
taantaaata acttcgtata gcatacatta tacgaagtta t               41

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 38
atgataactt cgtatagcat acattatacg aagttat                    37

<210> SEQ ID NO 39
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 39
aaagttatat aaaacgacat gcgtttcgta gatctaagga gatataaca       49

<210> SEQ ID NO 40
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 40
aattttatta atttgttatc gaatcataaa ttatttgtat agttcatc        48

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 41
catgcgtgtc gcatactatt actaataggc agcgaggat                  39

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 42
catgatcctc gctgcctatt agtaatagta tgcgacacg                  39
```